(12) United States Patent
Yu et al.

(10) Patent No.: US 11,948,296 B2
(45) Date of Patent: Apr. 2, 2024

(54) METHOD AND SYSTEM FOR ASSESSING FIBROSIS IN A TISSUE SAMPLE

(71) Applicant: Agency for Science, Technology and Research, Singapore (SG)

(72) Inventors: Hanry Yu, Singapore (SG); Yang Yu, Singapore (SG)

(73) Assignee: Agency for Science, Technology and Research, Singapore (SG)

(*) Notice: Subject to any disclaimer, the term of this patent is extended or adjusted under 35 U.S.C. 154(b) by 599 days.

(21) Appl. No.: 17/261,081

(22) PCT Filed: Jul. 30, 2019

(86) PCT No.: PCT/SG2019/050378
§ 371 (c)(1),
(2) Date: Jan. 18, 2021

(87) PCT Pub. No.: WO2020/027732
PCT Pub. Date: Feb. 6, 2020

(65) Prior Publication Data
US 2021/0319554 A1 Oct. 14, 2021

(30) Foreign Application Priority Data
Jul. 30, 2018 (SG) .......................... 10201806494Y

(51) Int. Cl.
*G06T 7/00* (2017.01)
*G06N 3/04* (2023.01)
(Continued)

(52) U.S. Cl.
CPC ............. *G06T 7/0012* (2013.01); *G06N 3/04* (2013.01); *G16H 10/40* (2018.01); *G16H 30/40* (2018.01);
(Continued)

(58) Field of Classification Search
CPC ......... G06T 7/0012; G06T 2207/20081; G06T 2207/20084; G06T 2207/30056;
(Continued)

(56) References Cited

U.S. PATENT DOCUMENTS 9,965,871 B1 * 5/2018 Li ..................... G06F 18/24323
10,580,130 B2 * 3/2020 Frangioni ............... G06T 11/60
(Continued)

FOREIGN PATENT DOCUMENTS

CN 107895368 A 4/2018
CN 108198170 A * 6/2018 ........... G06T 7/0012
(Continued)

OTHER PUBLICATIONS

International Search Report for International Application No. PCT/SG2019/050378 dated Oct. 9, 2019, pp. 1-5.
(Continued)

*Primary Examiner* — Khai M Nguyen
(74) *Attorney, Agent, or Firm* — Shackelford, Bowen, McKinley & Norton, LLP

(57) ABSTRACT

There is provided a method of assessing fibrosis in a tissue sample. The method includes: obtaining a stained image of a stained tissue sample, the stained tissue sample being stained in relation to collagen therein; producing a plurality of different types of collagen images based on the stained image, the plurality of different types of collagen images corresponding to a plurality of different types of collagen, respectively; determining a plurality of different types of collagen parameters based on the plurality of different types of collagen images using a deep neural network; and determining a degree of fibrosis in the stained tissue sample based on the plurality of different types of collagen parameters. The plurality of different types of collagen comprises portal collagen, fibrillary collagen and septal collagen. The differ-
(Continued)

ent types of collagen images are produced by determining if the collagen satisfies a predetermined size condition or a predetermined distance condition with respect to a boundary of the portal tracts and central veins.

20 Claims, 16 Drawing Sheets

(51) Int. Cl.
    *G16H 10/40*     (2018.01)
    *G16H 30/40*     (2018.01)
    *G16H 50/20*     (2018.01)

(52) U.S. Cl.
    CPC ... *G16H 50/20* (2018.01); *G06T 2207/20081* (2013.01); *G06T 2207/20084* (2013.01); *G06T 2207/30056* (2013.01)

(58) Field of Classification Search
    CPC ........ G16H 10/40; G16H 50/20; G16H 30/40; G06N 3/04
    See application file for complete search history.

(56) References Cited

U.S. PATENT DOCUMENTS

| | | | | |
|---|---|---|---|---|
| 2008/0015448 | A1* | 1/2008 | Keely | A61B 5/0068 600/562 |
| 2015/0339816 | A1* | 11/2015 | Yu | G06T 7/10 382/128 |
| 2021/0199582 | A1* | 7/2021 | Fereidouni | G01N 21/6428 |

FOREIGN PATENT DOCUMENTS

| | | |
|---|---|---|
| CN | 108230387 A | 6/2018 |
| WO | 2008039758 A2 | 4/2008 |
| WO | 2011123068 A1 | 10/2011 |
| WO | 2014109708 A1 | 7/2014 |
| WO | 2019077108 A2 | 4/2019 |

OTHER PUBLICATIONS

Written Opinion of the International Searching Authority for International Application No. PCT/SG2019/050378 dated Oct. 9, 2019, pp. 1-7.
Yu et al., "A Method and System for Assessing Fibrosis in a Tissue," translation of "Qualitative Pathology to Quantitative Features for Liver Disease Classification," 2012, pp. 1-86.
Yu et al., "Instaneous Virtual Biopsy for Liver Fibrosis Staging Using Second Harmonic Generation Microscopy," 2009, pp. 1-17.
Zhang et al., Artifical Neural Network Aided Non-Invasive Grading Evaluation of Hepatic Fibrosis by Duplex Ultrasonography, BMC Medical informatics & Decision Making, vol. 12, No. 55, 2012, pp. 1-6.
Hashem et al., "Accurate Prediction of Advanced Liver Fibrosis Using the Decision Tree Learning Algorithm in Chronic Hepatitis C Egyptian Patients," Gastroenterology Research and Practice, vol. 2016, Article ID 2636390, pp. 1-7.
Dowman et al., "Systematic Review: The Diagnosis and Staging of Non-Alcoholic Fatty Liver Disease and Non-Alcoholic Steatohepatitis," Alimentary Pharmacology and Therapeutics, vol. 33, 2011, pp. 525-540.
Knodell et al., "Formulation and Application of a Numerical Scoring System for Assessing Histological Activity in Asymptomatic Chronic Active Hepatitis," Hepatology, vol. 1, No. 5, 1981, pp. 431-435.
Peter J. Scheuer, "Classification of Chronic Viral Hepatitis: A Need for Reassessment," Journal of Hepatology,1991, vol. 13, pp. 372-374.

Bedossa et al., "An Algorithm for the Grading of Activity in Chronic Hepatitis C," Hepatology, vol. 24, 1996, pp. 289-293.
Ishak et al., "Histological Grading and Staging of Chronic Hepatitis," Journal of Hepatology, vol. 22, 1995, pp. 696-699.
Chen et al., "Machine-Learning-Based Classification of Real-Time Tissue Elastography for Hepatic Fibrosis in Patients with Chronic Hepatitis B," Computers in Biology and Medicine, vol. 89, 2017, pp. 18-23.
Xu et al., "qFibrosis: A Fully-Quantitative Innovative Method Incorporating Histological Features to Facilitate Accurate Fibrosis Scoring in Animal Model and Chronic Hepatitis B Patients," Journal of Hepatology, vol. 61, 2014, pp. 260-269.
Stanciu et al., "Experimenting Liver Fibrosis Diagnostic by Two Photon Excitation Microscopy and Bag-of-Features Image Classification," Scientific Reports, vol. 4, No. 4636, Apr. 10, 2014, pp. 1-12.
Shen et al., "Deep Learning in Medical Image Analysis," Annual Review of Biomedical Engineering, vol. 19, Jun. 21, 2017, pp. 221-248.
Rawat et al., "Deep Convolutional Neural Networks for Image Classification: A Comprehensive Review," Neural Computation, vol. 29, 2017, pp. 2352-2449.
Yasaka et al., "Liver Fibrosis: Deep Convolutional Neural Network for Staging by Using Gadoxetic Acid-Enhanced Hepatobiliary Phase MR Images," Radiology, vol. 287, No. 1, Apr. 2018, pp. 146-155.
Desautels et al., "Using Transfer Learning for Improved Mortality Prediction in a Data-Scarce Hospital Setting," Biomedical Informatics Insights, vol. 9, 2017, pp. 1-8.
Sharma et al., "Deep Convolutional Neural Networks for Automatic Classification of Gastric Carcinoma Using Whole Slide Images in Digital Histopathology," Computerized Medical Imaging and Graphics 61, 2017, pp. 2-13.
Shin et al., "Deep Convolutional Neural Networks for Computer-Aided Detection: CNN Architectures, Dataset Characteristics and Transfer Learning," IEEE Transactions on Medical Imaging, vol. 35, No. 5, May 2016, pp. 1285-1298.
Tai et al., "Fibro-C-Index: Comprehensive, Morphology-Based Quantification of Liver Fibrosis Using Second Harmonic Generation and Two-Photon Microscopy," Journal of Biomedical Optics, vol. 14, No. 4, pp. 1-10.
Bedossa et al., "Sampling Variability of Liver Fibrosis in Chronic Hepatitis C," Hepatology, vol. 38, 2003, pp. 1449-1457.
Chen et al., "Image Segmentation via Adaptive K-Mean Clustering and Knowledge-Based Morphological Operations with Biomedical Applications," IEEE Transactions on Image Processing, vol. 7, No. 12, Dec. 1998, pp. 1673-1683.
Krizhevsky et al., "ImageNet Classification with Deep Convolutional Neural Networks," Proceedings of the 25th International Conference on Neural Information Processing Systems—vol. I, Lake Tahoe, Nevada, 2012, pp. 1097-1105.
Lee et al., "Multinomial Logistic Regression Ensembles," Journal of Biopharmaceutical Statistics, vol. 23, 2013, pp. 681-694.
Wang et al., "Automated Biphasic Morphological Assessment of Hepatitis B-Related Liver Fibrosis Using Second Harmonic Generation Microscopy," Scientific Reports, vol. 5, 2015, pp. 1-12.
Standish et al., "An Appraisal of the Histopathological Assessment of Liver Fibrosis," Gut, vol. 55, 2006, pp. 569-578.
Chen et al., "Second Harmonic Generation Microscopy for Quantitative Analysis of Collagen Fibrilar Structure," Nature Protocols, vol. 7, No. 4, 2012, pp. 654-669.
Dilger et al., "Improved Pulmonary Nodule Classification Utilizing Quantitative Lung Parenchyma Features," Journal of Medical Imaging, vol. 2, No. 4, Oct.-Dec. 2015, pp. 1-10.
Sun et al., "New Classification of Liver Biopsy Assessment for Fibrosis in Chronic Hepatitis B Patients Before and After Treatment," Hepatology, vol. 65, No. 5, 2017, pp. 1438-1450.
Yu et al., "Deep Learning Enables Automated Scoring of Liver Fibrosis Stages," Scientific Reports, vol. 8, No. 1, Oct. 30, 2018, pp. 1-10.

\* cited by examiner

METHOD AND SYSTEM FOR ASSESSING FIBROSIS IN A TISSUE SAMPLE

CROSS-REFERENCE TO RELATED APPLICATION

This application claims the benefit of priority of Singapore Patent Application No. 10201806494Y, filed 30 Jul. 2018, the content of which being hereby incorporated by reference in its entirety for all purposes.

TECHNICAL FIELD

The present invention generally relates to a method and a system for assessing fibrosis in a tissue sample.

BACKGROUND

Fibrosis is the formation of excess fibrous connective tissue in an organ or tissue in a reparative or reactive process. As fibrosis is defined by the pathological accumulation of extracellular matrix (ECM) proteins, it results in scarring and thickening of the affected tissue. It is in essence an exaggerated wound healing response which interferes with normal organ function. The initial process of tissue repair can lead to a progressive irreversible fibrotic response if tissue injury is severe or repetitive, or if the wound healing response itself becomes deregulated. Therefore, it is desirable to assess the progression or regression of the degree of fibrosis in the affected tissue. For example, in a diseased liver, histopathological examination of tissue samples is preferred for staging of the liver fibrosis and remains as the 'gold standard' in the assessment of liver fibrosis at present. Histopathological features such as excessive accumulation of ECM (particularly collagen) and/or parenchymal extinction are incorporated into descriptive or semi-quantitative scoring systems for disease staging. Examples of scoring systems include the Knodell histological activity index (HAI), Scheuer, Ishak, Metavir, and Ishak-modified systems. The scores may be used to monitor the progression or regression of the diseased liver. However, these scoring systems are inherently semi-quantitative and subject to intra- and inter-observer variability. For example, the Metavir scoring system, commonly practiced in the clinical settings, is a categorical assignment based largely on observed architectural changes and fibrotic changes, instead of quantitative measurement of fibrosis content. Further, inter- and intra-observer and staining variations may generate errors in disease staging.

With the development of both mode-locked lasers and highly sensitive optical sensors, non-linear optical microscopy (such as those based on multi-photon excitation fluorescence and multi-harmonic generation) has made stain-free imaging-based diagnosis a feasible approach. Further, with the generation of large amounts of data using these imaging modalities, several groups have explored the use of machine learning-based algorithms for the scoring of liver fibrosis stages. For example, systems using machine learning-based algorithms have previously been developed to build diagnostic tools for improved liver fibrosis quantification and scoring. These algorithms include artificial neural networks (ANN), multinomial logistic regression (MLR), support vector machines (SVM), and random forests (RF). For example, machine-learning may be used for the prediction, classification and assessment of liver fibrosis/cirrhosis, and response to therapy in hepatitis B and C patients. However, most of previous machine learning-based approaches rely on the multi-photon microscopy technique for the assessment of liver fibrosis/cirrhosis, such as second-harmonic generation (SHG) and two-photon-excited fluorescence (TPEF), which is not commonly available in the clinical settings. Further, in addition to having a limited number of extracted features, the algorithms require feature extraction using domain knowledge from histo-pathological perspectives for the images prior to modeling and classification. In addition, the utility of the various algorithms remains unclear as they are usually case dependent and none of existing algorithms are fully automated since they would require image segmentation and feature extraction by computer algorithms guided by the pathologist in some stage.

A need therefore exists to provide tissue fibrosis assessment methods/systems that seek to overcome, or at least ameliorate, one or more of the deficiencies in conventional tissue fibrosis assessment methods/systems. It is against this background that the present invention has been developed.

SUMMARY

According to a first aspect of the present invention, there is provided a method of assessing fibrosis in a tissue sample using at least one processor, the method comprising:
  obtaining a stained image of a stained tissue sample, the stained tissue sample being stained in relation to collagen therein;
  producing a plurality of different types of collagen images based on the stained image, the plurality of different types of collagen images corresponding to a plurality of different types of collagen, respectively;
  determining a plurality of different types of collagen parameters based on the plurality of different types of collagen images using a deep neural network; and
  determining a degree of fibrosis in the stained tissue sample based on the plurality of different types of collagen parameters.

According to a second aspect of the present invention, there is provided a system for assessing fibrosis in a tissue sample, the system comprising:
  a memory; and
  at least one processor communicatively coupled to the memory and configured to:
    obtain a stained image of a stained tissue sample, the stained tissue sample being stained in relation to collagen therein;
    produce a plurality of different types of collagen images based on the stained image, the plurality of different types of collagen images corresponding to a plurality of different types of collagen, respectively;
    determine a plurality of different types of collagen parameters based on the plurality of different types of collagen images using a deep neural network; and
    determine a degree of fibrosis in the stained tissue sample based on the plurality of different types of collagen parameters.

According to a third aspect of the present invention, there is provided a computer program product, embodied in one or more non-transitory computer-readable storage mediums, comprising instructions executable by at least one processor to perform a method of assessing fibrosis in a tissue sample, the method comprising:
  obtaining a stained image of a stained tissue sample, the stained tissue sample being stained in relation to collagen therein;

producing a plurality of different types of collagen images based on the stained image, the plurality of different types of collagen images corresponding to a plurality of different types of collagen, respectively;

determining a plurality of different types of collagen parameters based on the plurality of different types of collagen images using a deep neural network; and determining a degree of fibrosis in the stained tissue sample based on the plurality of different types of collagen parameters.

BRIEF DESCRIPTION OF THE DRAWINGS

Embodiments of the present invention will be better understood and readily apparent to one of ordinary skill in the art from the following written description, by way of example only, and in conjunction with the drawings, in which:

FIG. 3 depicts an example computer system which the system according to various embodiments of the present invention may be embodied in;

DETAILED DESCRIPTION

Various embodiments of the present invention provide a method (computer-implemented method) and a system (including a memory and at least one processor communicatively coupled to the memory) for assessing fibrosis (e.g., determining a degree or level of fibrosis) in a tissue sample. In various embodiments, a fully automated technique for assessing (e.g., staging) fibrosis based on an image (which may herein be referred to as a "stained image") of a stained tissue sample is provided. The tissue sample, for example, may be extracted by biopsy from various anatomical locations of an animal or human body. For example, the tissue sample may be extracted from an anatomical structure (such as a liver) in which fibrosis of the anatomical structure is to be assessed or determined. It will be understood by a person skilled in the art that tissue samples extracted by biopsy from other anatomical structures or locations of the animal or human body are within the scope of the present invention, such as but not limited to, lungs, skin, stomach, small and large intestines, etc. Accordingly, fibrosis in the anatomical location may be assessed, for example, to determine a degree (e.g., extent, level or stage) of fibrosis in the anatomical structure. For example, the degree of fibrosis determined may be used for the prediction, classification, diagnosis, assessment of progression or regression of a diseased anatomical structure in response to treatment of fibrosis in tissue. In various embodiments, the fully automated technique for staging fibrosis in an anatomical structure or location may use images of existing stained tissue samples (e.g., tissue samples which have been stained using dyes to provide details of the tissue structure/morphology).

Figure 1:
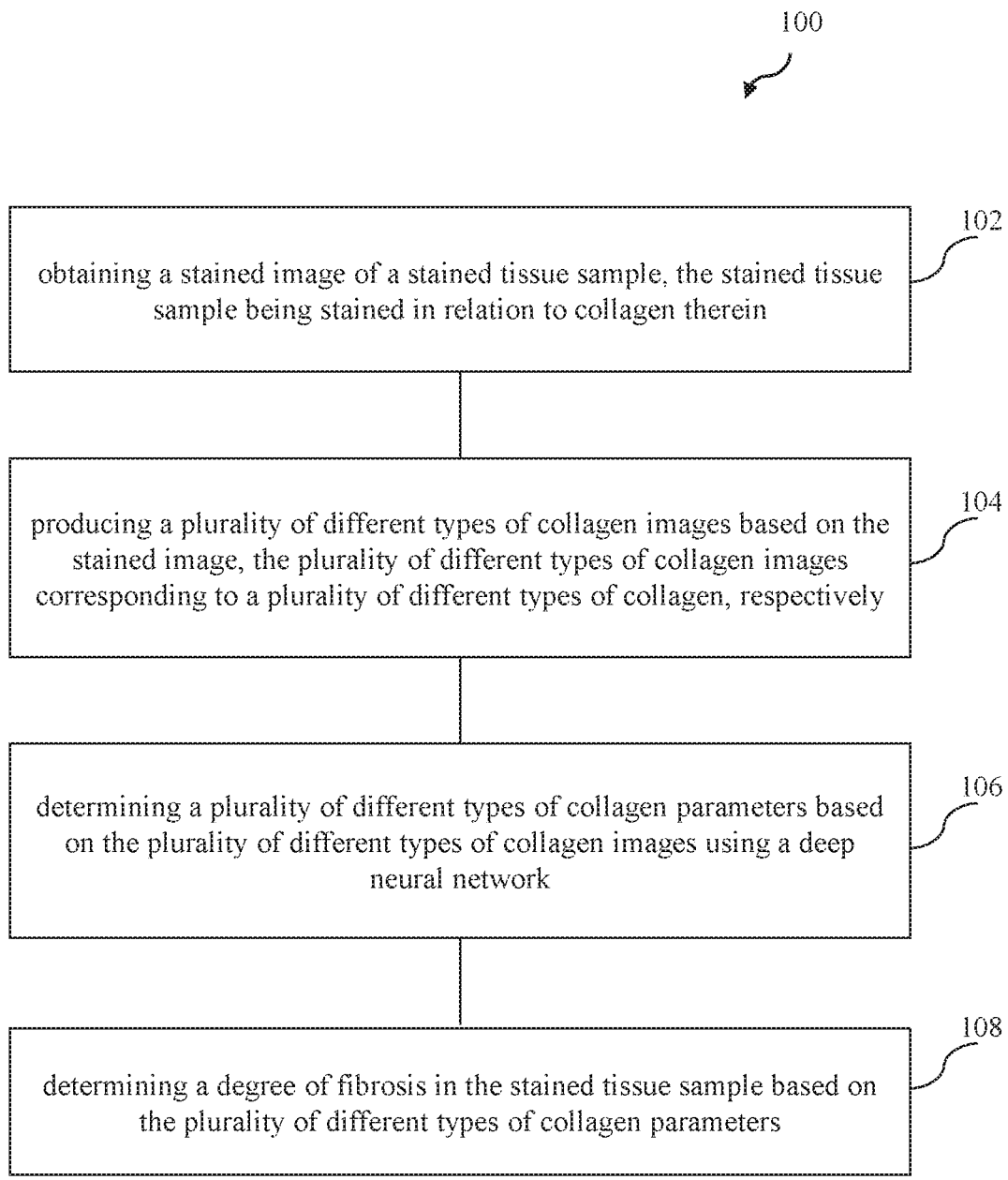
FIG. 1 depicts a schematic flow diagram of a method for assessing fibrosis in a tissue sample using at least one processor according to various embodiments of the present invention.

FIG. 1 depicts a schematic flow diagram of a method 100 (computer-implemented method) for assessing fibrosis in a tissue sample using at least one processor according to various embodiments of the present invention. The method 100 comprises obtaining (at 102) a stained image of a stained tissue sample, the stained tissue sample being stained in relation to collagen therein; producing (at 104) a plurality of different types of collagen images based on the stained image, the plurality of different types of collagen images corresponding to a plurality of different types of collagen, respectively; determining (at 106) a plurality of different types of collagen parameters based on the plurality of different types of collagen images using a deep neural network; and determining (at 108) a degree of fibrosis in the stained tissue sample based on the plurality of different types of collagen parameters.

In relation to 102, for example, the tissue sample may be extracted from the anatomical location of the animal or human body to be assessed. In various embodiments, the tissue sample may be stained in relation to collagen in the tissue sample. For example, the tissue sample may be stained using various existing staining techniques to highlight relevant tissue morphology or features in the tissue including the collagen for assessing fibrosis in the tissue. An image (stained image) of the stained tissue sample may be obtained and processed to determine a degree of fibrosis in the stained tissue sample. A stained image as described herein refers to an image of a stained tissue sample, which may be obtained from an image capturing device. In various embodiments, the image capturing device may produce a stained image of a stained tissue sample and at least one processor may then obtain (or receive) the stained image for processing to assess fibrosis in the stained tissue sample. As a non-limiting example, the image capturing device may be, or include, a microscope, a tissue scanner or combinations thereof.

In relation to 104, for example, the stained image may be processed (or pre-processed) to identify and differentiate (or separate or segment) the plurality of different types of collagen captured in the stained image. For example, the stained image may be processed to categorize the collagen in the stained image into different types (e.g., different categories or classifications) according to their histo-pathological properties. For example, three main different types of collagen may be identified for the assessment of fibrosis in an anatomical structure or location, such as in the assessment of liver fibrosis. In various embodiments, as will be described later in various example embodiments of the present invention, the plurality of different types of collagen may comprise portal collagen, fibrillar collagen and septal collagen. For example, the portal collagen, fibrillar collagen and septal collagen may be identified or utilized in the assessment of liver fibrosis. It is understood that the present invention is not limited to the above-mentioned three different types of collagen and the assessment of liver fibrosis. For example, other types of collagen and/or other number (e.g., more than three) of types of collagen may be obtained or identified as desired or as appropriate. For example, other types and number of types of pathologically-relevant features such as other collagen areas in the tissue based on morphology or structure and/or spatially related features may also be used for the categorization of the types of collagen for the assessment of fibrosis in the anatomical structure. In another example implementation, different types of collagen content may be identified from the stained image in intra-cirrhosis detection, for example, to facilitate differentiating the progressive/regressive distribution pattern of collagen fibers for further defining the sub-category of cirrhosis.

In various embodiments, the above-mentioned producing the plurality of different types of collagen images comprises producing a first image corresponding to (e.g., in relation to or representative of) tissue in the stained image, and producing a second image corresponding to (e.g., in relation to or representative of) collagen in the stained image. In various embodiments, the first and second images may be produced based on a clustering technique such as K-mean clustering. For example, the stained image may be processed to separate the collagen from the tissue (and/or background) using K-mean clustering based on their pixels' distribution in Lab/RGB/HSV space.

In various embodiments, the above-mentioned producing the plurality of different types of collagen images further comprises producing a third image corresponding to (e.g., in relation to or representative of) portal tracts and central veins in the first image. For example, as the first image records signals of the tissue (e.g., hepatocyte cells), the portal tracts and central veins may be represented by empty spaces. In various embodiments, pixels corresponding to portal tracts and central veins may be separated (or identified) based on their intensity values. The third image may be produced based on the identified pixels corresponding to portal tracts and central veins.

In various embodiments, the above-mentioned producing a plurality of different types of collagen images further comprises producing a first binarized image based on the second image, producing a second binarized image based on the third image, and producing the plurality of different types of collagen images based on the first and second binarized images. In relation to producing the first binarized image based on the second image, the second image may be processed using contrast enhancement to enhance the collagen intensity and converted to the first binarized image using adaptive thresholding. Additionally, in some case, morphological closing may be used to connect fragmented collagen fibers and/or a despeckle filter may be used to remove noise. In relation to producing the second binarized image based on the third image, various operations, including but not limited to, Otsu-thresholding, morphological opening/closing and hole-filing operations may be performed, for example, to smooth spaces. Additionally, spaces smaller than a predetermined size (e.g., size of one hepatocyte) and spaces with large major-axis-length to minor-axis-length (e.g., assumed to be sinusoidal spaces) may be removed.

In various embodiments, the plurality of different types of collagen images comprises a first type, a second type, and a third type of collagen images, and the above-mentioned producing the plurality of different types of collagen images based on the first and second binarized images comprises producing the first type of collagen image based on collagen in the first binarized image satisfying a predetermined size condition, producing the second type of collagen image based on collagen in the first binarized image satisfying a predetermined distance condition with respect to a boundary of the portal tracts and the central veins in the second binarized image, and producing the third type of collagen image based on collagen in the first binarized image that does not satisfy the predetermined size condition and the predetermined distance condition. In a non-limiting example, the predetermined size condition may be collagen fibers having areas less than a predetermined value (e.g., 10 $um^2$) in the first binarized image. For example, collagen satisfying such predetermined size condition may represent fragmented collagen distributed in the tissue. In a non-limiting example, the predetermined distance condition with respect to a boundary of the portal tracts and the central veins in the second binarized image may be a predetermined distance threshold, such as a cut-off distance for example, determined with respect to the boundary of the portal tracts and the central veins. For example, pixels from the boundary of the portal tracts or central veins may be first selected, and a cut-off distance may be determined (or chosen) to dilate those selected pixels. The second type of collagen image may be produced based on collagen in the first binarized image which are within the determined cut-off distance. The first type of collagen image may correspond to a first type collagen, the second type of collagen image may correspond to a second type collagen, and the third type of collagen image may correspond to a third type collagen. In various embodiments, the first type of collagen may be fibrillar collagen, the second type of collagen may be portal collagen, and the third type of collagen may be septal collagen.

In relation to 106, in various embodiments, the plurality of different types of collagen parameters each comprises a quantitative fibrosis value in relation to the corresponding type of collagen of the plurality of different types of collagen in the stained tissue sample. In various embodiments, the quantitative fibrosis value of a corresponding type of collagen may be a fibrosis index for that type of collagen in the stained tissue sample. For example, for each type of collagen image of the plurality of different types of collagen images, the deep neural network may be used to extract collagen features for the corresponding type of collagen in the collagen image to determine the respective collagen parameter. A respective collagen parameter may be accordingly determined for that type of collagen.

In various embodiments, the deep neural network may include a plurality of deep neural sub-networks, such as a plurality of deep convolutional neural network (DCNN) to determine the plurality of different types of collagen parameters based on the plurality of different types of collagen images. In various embodiments, the deep neural network comprises a plurality of deep neural sub-networks corresponding to the plurality of different types of collagen respectively. Each deep neural sub-network used may be a pretrained DCNN. The plurality of deep neural sub-networks may be trained separately for respective types of collagen to produce or determine a respective collagen parameter for a corresponding type of collagen. In other words, each deep neural sub-network of the plurality of deep neural sub-networks may be trained for a particular type of collagen and used to determine a respective collagen parameter for that type of collagen based on a collagen image corresponding to that type of collagen. In various embodiments, each deep neural sub-network may be pre-trained based on a learning transfer technique. In various embodiments, each deep neural sub-network may be an adapted AlexNet-CNN. In various embodiments, each deep neural sub-network of the plurality of deep neural sub-networks may be configured to output a quantitative fibrosis value in relation to a respective type of collagen based on the collagen image corresponding to that type of collagen. For example, three CNNs may be trained separately to produce the first quantitative fibrosis value corresponding to the first type of collagen, the second quantitative fibrosis value corresponding to the second type of collagen and the third quantitative fibrosis value corresponding to the third type of collagen, respectively.

In relation to 108, in various embodiments, the degree of fibrosis in the tissue sample may be determined based on the different types of collagen parameters using a multinomial logistic regression. For example, the degree of fibrosis in the tissue sample may be determined based on determined collagen parameters of the respective portal collagen, the fibrillar collagen and the septal collagen. In various embodiments, the determined degree of fibrosis in the stained tissue sample may be a final fibrosis index (which may be referred to herein as sqFibrosis index). For example, a single evaluation metric may be determined from the plurality of different types of collagen parameters for assessment of fibrosis in the tissue sample. For example, the single evaluation metric may be determined based on the first quantitative fibrosis value, the second quantitative fibrosis value and the third quantitative fibrosis value using logistic regression. The final fibrosis index combines predicted results (plurality of different types of collagen parameters) from the plurality of different types of collagen. For example, statistical analysis of features of the respective type collagen may be performed to determine the final fibrosis index. The final fibrosis index may be set according to the Metavir scoring system F0-F4 and may be used as the final stage indicator of fibrosis progression. In other words, a single index (sqFibrosis) may be generated on the tissue level for fibrosis evaluation from F0-F4. The final fibrosis index may be generated amongst a predefined set of final fibrosis indices according to Metavir scoring, which may be an indicator of stage of fibrosis in the tissue (tissue sample).

Accordingly, various embodiments of the present invention advantageously provide a fully automated technique for staging or scoring of fibrosis in a tissue sample. In various example embodiments, existing stained tissue samples may be used for assessing fibrosis therein. Further, various embodiments of the present invention enable disease diagnosis even with limited numbers of biopsy samples or clinical information.

Figure 2:
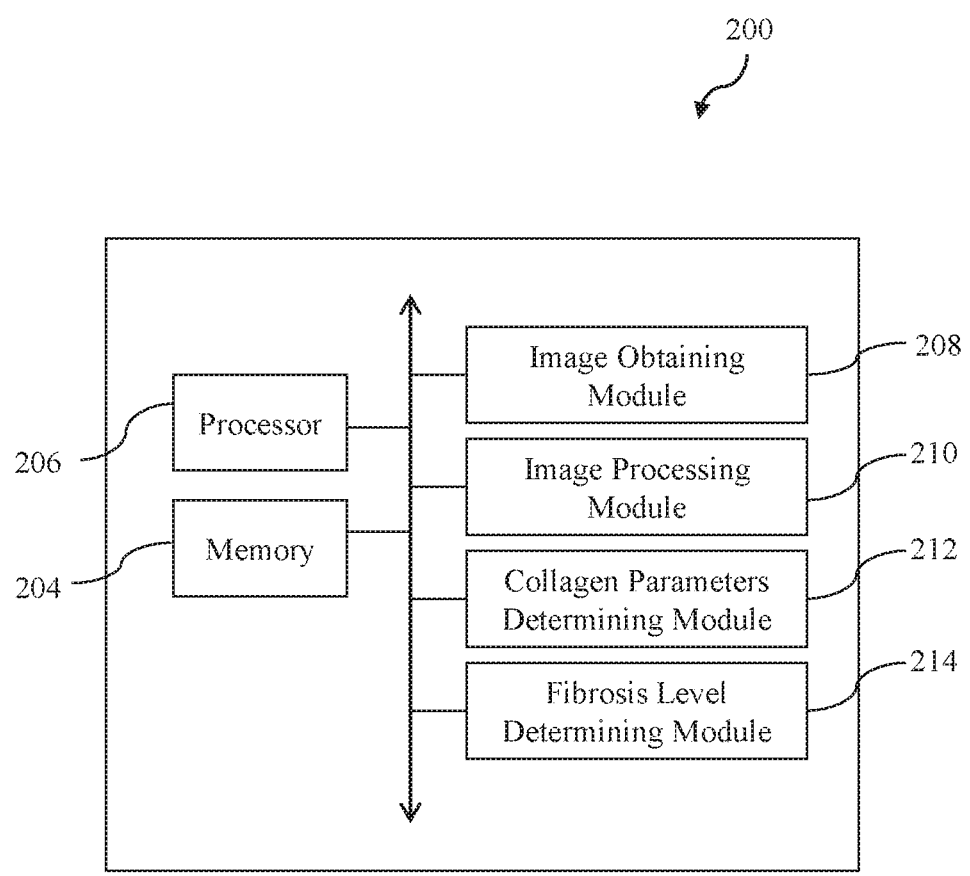
FIG. 2 depicts a schematic block diagram of a system for assessing fibrosis in a tissue sample according to various embodiments of the present invention, such as corresponding to the method shown in FIG. 1.

FIG. 2 depicts a schematic block diagram of a system 200 for assessing fibrosis in a tissue sample according to various embodiments of the present invention, such as corresponding to the method 100 for assessing fibrosis in a tissue sample as described hereinbefore according to various embodiments of the present invention.

The system 200 comprises a memory 204, and at least one processor 206 communicatively coupled to the memory 204 and configured to: obtain a stained image of a stained tissue sample, the stained tissue sample being stained in relation to collagen therein; produce a plurality of different types of collagen images based on the stained image, the plurality of different types of collagen images corresponding to a plurality of different types of collagen, respectively; determine a plurality of different types of collagen parameters based on the plurality of different types of collagen images using a deep neural network; and determine a degree of fibrosis in the stained tissue sample based on the plurality of different types of collagen parameters.

It will be appreciated by a person skilled in the art that the at least one processor 206 may be configured to perform the required functions or operations through set(s) of instructions (e.g., software modules) executable by the at least one processor 206 to perform the required functions or operations. Accordingly, as shown in FIG. 2, the system 200 may further comprise an image obtaining module (or circuit) 208 configured to obtain a stained image of a stained tissue sample; an image processing module (or circuit) 210 configured to produce a plurality of different types of collagen images based on the stained image; a collagen parameters determining module (or circuit) 212 configured to determine a plurality of different types of collagen parameters based on the plurality of different types of collagen images using a deep neural network; and a fibrosis level determining module (or circuit) 214 configured to determine a degree of fibrosis in the stained tissue sample based on the plurality of different types of collagen parameters.

It will be appreciated by a person skilled in the art that the above-mentioned modules (or circuits) are not necessarily separate modules, and two or more modules may be realized by or implemented as one functional module (e.g., a circuit or a software program) as desired or as appropriate without deviating from the scope of the present invention. For example, the image obtaining module 208, the image processing module 210, the collagen parameters determining module 212, and/or the fibrosis level determining module 214 may be realized (e.g., compiled together) as one executable software program (e.g., software application or simply referred to as an "app"), which for example may be stored in the memory 204 and executable by the at least one processor 206 to perform the functions/operations as described herein according to various embodiments.

In various embodiments, the system 200 corresponds to the method 100 as described hereinbefore with reference to FIG. 1, therefore, various functions/operations configured to be performed by the least one processor 206 may correspond to various steps or operations of the method 100 described hereinbefore according to various embodiments, and thus need not be repeated with respect to the system 200 for clarity and conciseness. In other words, various embodiments described herein in context of the methods are analogously valid for the respective systems (e.g., which may also be embodied as devices).

For example, in various embodiments, the memory 204 may have stored therein the image obtaining module 208, the image processing module 210, the collagen parameters determining module 212, and/or the fibrosis level determining module 214, which respectively correspond to various steps or operations of the method 100 as described hereinbefore, which are executable by the at least one processor 206 to perform the corresponding functions/operations as described herein.

A computing system, a controller, a microcontroller or any other system providing a processing capability may be provided according to various embodiments in the present disclosure. Such a system may be taken to include one or more processors and one or more computer-readable storage mediums. For example, the system 200 described hereinbefore may include a processor (or controller) 206 and a computer-readable storage medium (or memory) 204 which are for example used in various processing carried out therein as described herein. A memory or computer-readable storage medium used in various embodiments may be a volatile memory, for example a DRAM (Dynamic Random Access Memory) or a non-volatile memory, for example a PROM (Programmable Read Only Memory), an EPROM (Erasable PROM), EEPROM (Electrically Erasable PROM), or a flash memory, e.g., a floating gate memory, a charge trapping memory, an MRAM (Magnetoresistive Random Access Memory) or a PCRAM (Phase Change Random Access Memory).

In various embodiments, a "circuit" may be understood as any kind of a logic implementing entity, which may be special purpose circuitry or a processor executing software stored in a memory, firmware, or any combination thereof. Thus, in an embodiment, a "circuit" may be a hard-wired logic circuit or a programmable logic circuit such as a programmable processor, e.g., a microprocessor (e.g., a Complex Instruction Set Computer (CISC) processor or a Reduced Instruction Set Computer (RISC) processor). A "circuit" may also be a processor executing software, e.g., any kind of computer program, e.g., a computer program using a virtual machine code, e.g., Java. Any other kind of implementation of the respective functions which will be described in more detail below may also be understood as a "circuit" in accordance with various alternative embodiments. Similarly, a "module" may be a portion of a system according to various embodiments in the present invention and may encompass a "circuit" as above, or may be understood to be any kind of a logic-implementing entity therefrom.

Some portions of the present disclosure are explicitly or implicitly presented in terms of algorithms and functional or symbolic representations of operations on data within a computer memory. These algorithmic descriptions and functional or symbolic representations are the means used by those skilled in the data processing arts to convey most effectively the substance of their work to others skilled in the art. An algorithm is here, and generally, conceived to be a self-consistent sequence of steps leading to a desired result. The steps are those requiring physical manipulations of physical quantities, such as electrical, magnetic or optical signals capable of being stored, transferred, combined, compared, and otherwise manipulated.

Unless specifically stated otherwise, and as apparent from the following, it will be appreciated that throughout the present specification, discussions utilizing terms such as "determining", "obtaining", "producing", or the like, refer to the actions and processes of a computer system, or similar electronic device, that manipulates and transforms data represented as physical quantities within the computer system into other data similarly represented as physical quantities within the computer system or other information storage, transmission or display devices.

The present specification also discloses a system (which may also be embodied as a device or an apparatus) for performing the operations/functions of the methods described herein. Such a system may be specially constructed for the required purposes, or may comprise a general purpose computer or other device selectively activated or reconfigured by a computer program stored in the computer. The algorithms presented herein are not inherently related to any particular computer or other apparatus. Various general-purpose machines may be used with computer programs in accordance with the teachings herein. Alternatively, the construction of more specialized apparatus to perform the required method steps may be appropriate.

In addition, the present specification also at least implicitly discloses a computer program or software/functional module, in that it would be apparent to the person skilled in the art that the individual steps or operations of the methods described herein may be put into effect by computer code. The computer program is not intended to be limited to any particular programming language and implementation thereof. It will be appreciated that a variety of programming languages and coding thereof may be used to implement the teachings of the disclosure contained herein. Moreover, the computer program is not intended to be limited to any particular control flow. There are many other variants of the computer program, which can use different control flows without departing from the scope of the invention. It will be appreciated by a person skilled in the art that various modules described herein (e.g., the image obtaining module 208, the image processing module 210, the collagen parameters determining module 212, and/or the fibrosis level determining module 214) may be software module(s) realized by computer program(s) or set(s) of instructions executable by a computer processor to perform the required functions, or may be hardware module(s) being functional hardware unit(s) designed to perform the required functions. It will also be appreciated that a combination of hardware and software modules may be implemented.

Furthermore, one or more of the steps or operations of a computer program/module or method described herein may be performed in parallel rather than sequentially. Such a computer program may be stored on any computer readable medium. The computer readable medium may include storage devices such as magnetic or optical disks, memory chips, or other storage devices suitable for interfacing with a general-purpose computer. The computer program when loaded and executed on such a general-purpose computer effectively results in an apparatus that implements the steps or operations of the methods described herein.

In various embodiments, there is provided a computer program product, embodied in one or more computer-readable storage mediums (non-transitory computer-readable storage medium), comprising instructions (e.g., the image obtaining module 208, the image processing module 210, the collagen parameters determining module 212, and/or the fibrosis level determining module 214) executable by one or more computer processors to perform a method 100 for assessing fibrosis in a tissue sample as described hereinbefore with reference to FIG. 1. Accordingly, various computer programs or modules described herein may be stored in a computer program product receivable by a system (e.g., a computer system or an electronic device) therein, such as the system 200 as shown in FIG. 2, for execution by at least one processor 206 of the system 200 to perform the required or desired functions.

The software or functional modules described herein may also be implemented as hardware modules. More particularly, in the hardware sense, a module is a functional hardware unit designed for use with other components or modules. For example, a module may be implemented using discrete electronic components, or it can form a portion of an entire electronic circuit such as an Application Specific Integrated Circuit (ASIC). Numerous other possibilities exist. Those skilled in the art will appreciate that the software or functional module(s) described herein can also be implemented as a combination of hardware and software modules.

Figure 3:
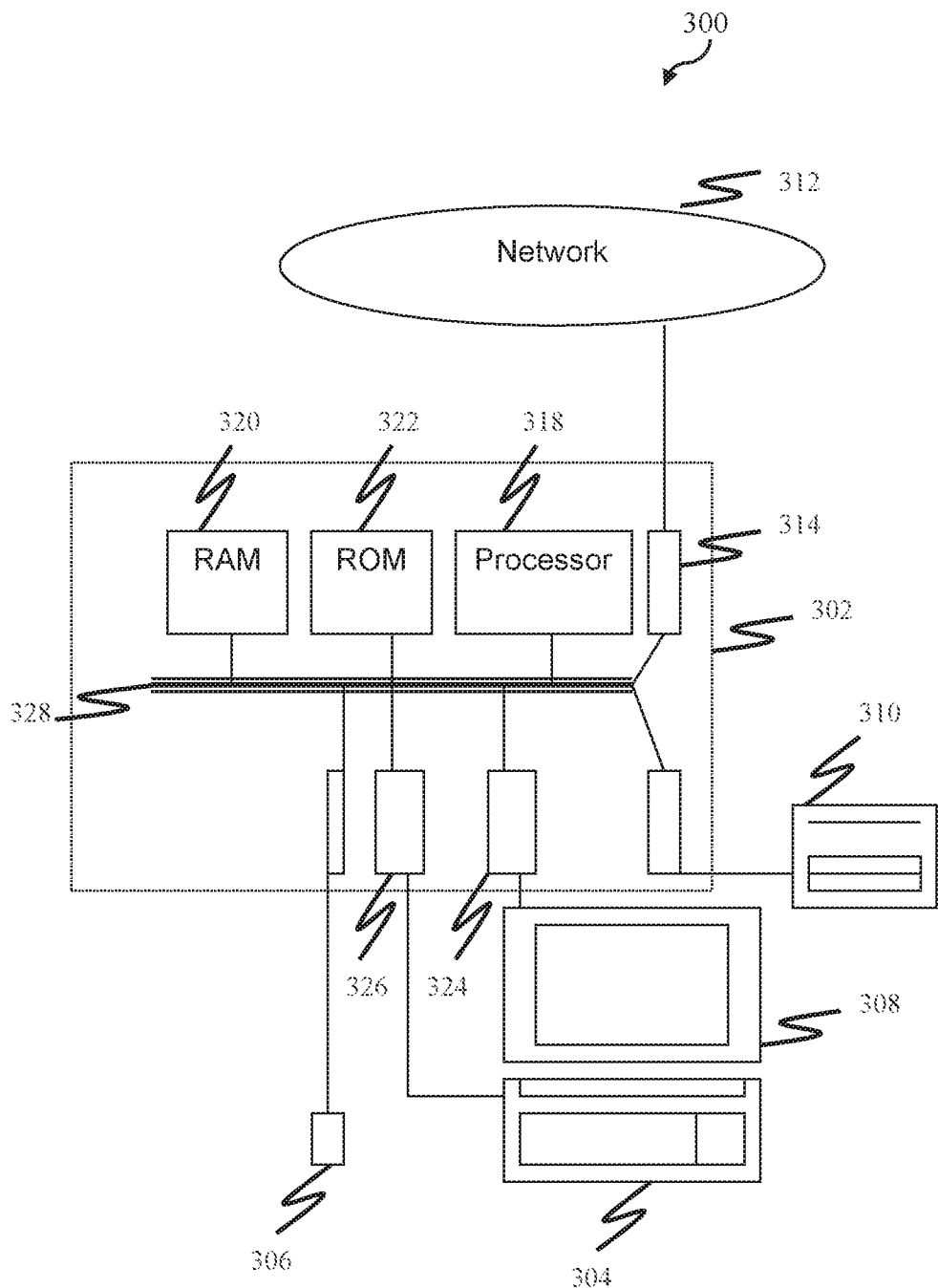

In various embodiments, the above-mentioned computer system may be realized by any computer system (e.g., portable or desktop computer system), such as a computer system 300 as schematically shown in FIG. 3 as an example only and without limitation. Various methods/operations or functional modules (e.g., the image obtaining module 208, the image processing module 210, the collagen parameters determining module 212, and/or the fibrosis level determining module 214) may be implemented as software, such as a computer program being executed within the computer system 300, and instructing the computer system 300 (in particular, one or more processors therein) to conduct the methods/functions of various embodiments described herein. The computer system 300 may comprise a computer module 302, input modules, such as a keyboard 304 and a mouse 306, and a plurality of output devices such as a display 308, and a printer 310. The computer module 302 may be connected to a computer network 312 via a suitable transceiver device 314, to enable access to e.g. the Internet or other network systems such as Local Area Network (LAN) or Wide Area Network (WAN). The computer module 302 in the example may include a processor 318 for executing various instructions, a Random Access Memory (RAM) 320 and a Read Only Memory (ROM) 322. The computer module 302 may also include a number of Input/Output (I/O) interfaces, for example I/O interface 324 to the display 308, and I/O interface 326 to the keyboard 304. The components of the computer module 302 typically communicate via an interconnected bus 328 and in a manner known to the person skilled in the relevant art.

It will be appreciated by a person skilled in the art that the terminology used herein is for the purpose of describing various embodiments only and is not intended to be limiting of the present invention. As used herein, the singular forms "a", "an" and "the" are intended to include the plural forms as well, unless the context clearly indicates otherwise. It will be further understood that the terms "comprises" and/or "comprising", or the like such as "includes" and/or "including", when used in this specification, specify the presence of stated features, integers, steps, operations, elements, and/or components, but do not preclude the presence or addition of one or more other features, integers, steps, operations, elements, components, and/or groups thereof.

In order that the present invention may be readily understood and put into practical effect, various example embodiments of the present invention will be described hereinafter by way of examples only and not limitations. It will be appreciated by a person skilled in the art that the present invention may, however, be embodied in various different forms or configurations and should not be construed as limited to the example embodiments set forth hereinafter. Rather, these example embodiments are provided so that this disclosure will be thorough and complete, and will fully convey the scope of the present invention to those skilled in the art.

In particular, for better understanding of the present invention and without limitation or loss of generality, various example embodiments of the present invention will now be described with respect to assessing fibrosis in a liver tissue extracted from a rat. For example, a stained image of a stained tissue sample may be obtained with respect to that of a liver tissue sample extracted from a fibrosis-induced liver of a rat, and which is collagen-stained. The stained image of the stained biopsy tissue sample may be assessed to determine a degree of fibrosis in the fibrosis-induced liver of the rat. However, it will be appreciated by a person skilled in the art that the present invention is not limited to assessing fibrosis in the tissue sample extracted from a liver, and the method for assessing fibrosis in the tissue sample as disclosed herein according to various embodiments may be applied to assess fibrosis in a tissue sample from various other types of anatomical locations of an animal or human body, such as but not limited to, lung, stomach, small and large intestines, etc., using pathological staining.

In various example embodiments, a stained image of a stained tissue sample may be processed to identify and categorize a plurality of different types of collagen in the tissue sample based on their histo-pathological properties. In various example embodiments, the plurality of different types of collagen may include portal collagen, fibrillar collagen and septal collagen. For example, the stained image may be processed to categorize the collagen fiber to the three different types. Other number of types and/or other types of collagen may be categorized depending on the type of tissue fibrosis being assessed.

Figure 4:
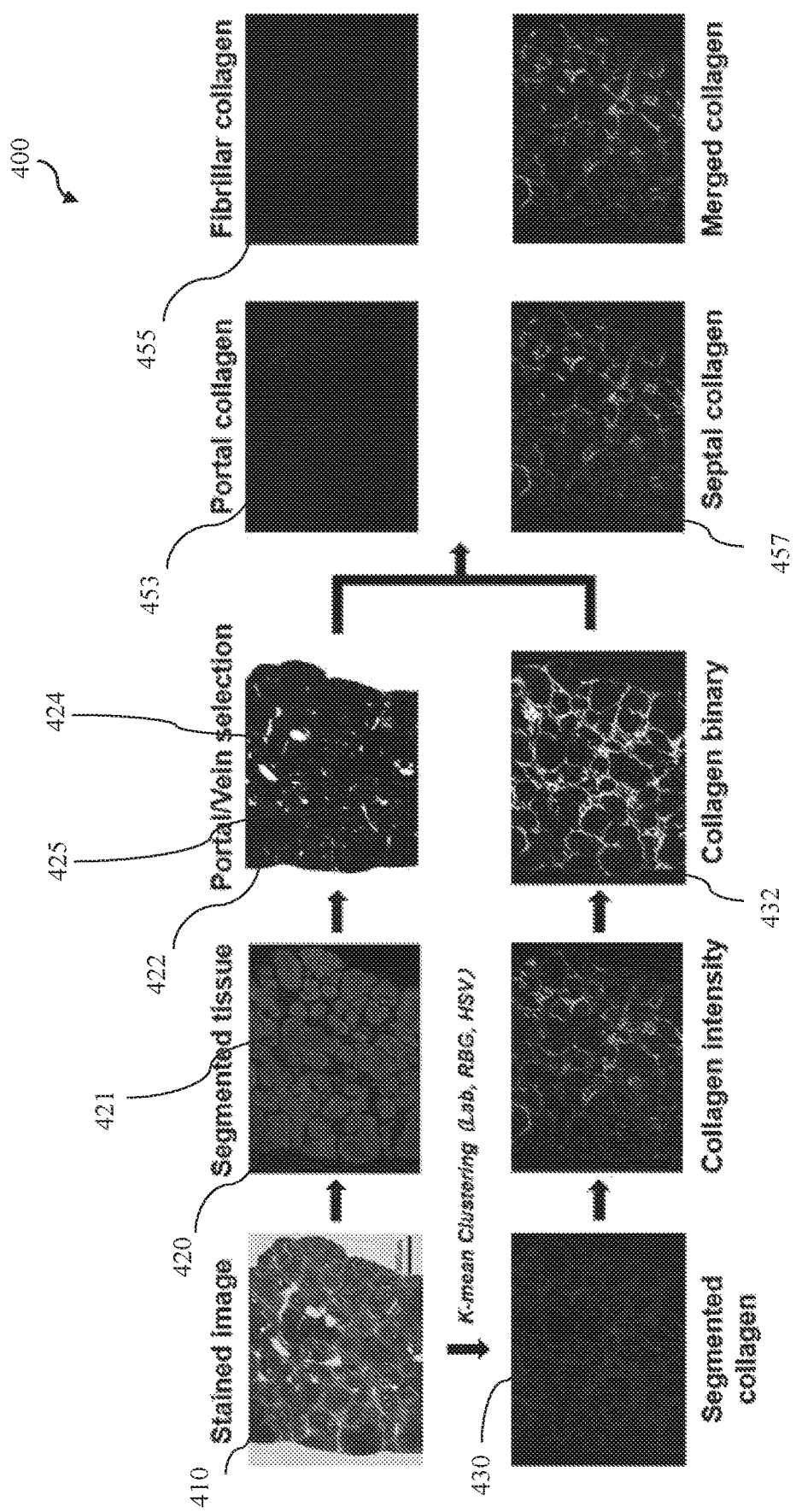
FIG. 4 illustrates an exemplary schematic for processing (or pre-processing) a stained image of a stained tissue sample to produce a plurality of different types of collagen images.

FIG. 4 illustrates an exemplary schematic for processing (or pre-processing) 400 the stained image of the stained tissue sample to produce a plurality of different types of collagen images. In various example embodiments, the stained tissue sample may be stained in relation to collagen therein.

In various example embodiments, the stained image of the stained tissue sample 410 may be obtained from an image capturing device. In various example embodiments, the image capturing device may be, or include, a bright field microscope for capturing the image of a stained tissue sample on a slide. Other image capturing device, such as a tissue scanner, may be used for obtaining the stained image.

In various example embodiments, the stained image may be separated into different categories of the stained image including background, tissue and collagen fibers to produce a first image 420 corresponding to tissue in the stained image and a second image 430 corresponding to collagen in the stained image. For example, collagen and tissue may be identified and extracted from the stained image based on a clustering technique such as K-mean clustering in a non-limiting example. For example, Chen, C. W., Luo, J. & Parker, K. J. Image segmentation via adaptive K-mean clustering and knowledge-based morphological operations with biomedical applications. *IEEE transactions on image processing: a publication of the IEEE Signal Processing Society* 7, 1673-1683, doi:10.1109/83.730379 (1998), discloses a technique of image segmentation based on K-mean clustering which may be implemented to identify and extract collagen and tissue from the stained image, the content of which being hereby incorporated by reference in its entirety for all purposes. For example, collagen and tissue may be identified and extracted from the stained image through K-mean clustering based on distribution of pixels representing the tissue and collagen fibers in Lab/RGB/HSV space.

For example, a clustering technique, such as K-mean clustering, may be used to determine the natural spectral groupings present in a data set. During such procedure, a predefined number of clusters may be set (e.g., the desired number of clusters to be located in the data may be accepted from an analyst). The technique may be initiated with arbitrarily located seeds for a plurality of cluster means corresponding to the predefined number of clusters respectively. Subsequently, in a first operation, each pixel in the stained image may be assigned to a closest cluster mean. In a second operation, a revised mean vector may be computed for each cluster. The first and second operations may be iterated. The iterations on the first and second operations may be continued until a predefined criteria is met. In a non-limiting example, the predefined criteria may be where the plurality of cluster means do not change between iterations. The efficiency of clustering, for example, may be determined by the clustering algorithms used for unsupervised classification of remote sensing data.

In various example embodiments, a color-based K-means clustering technique may be performed as follows. First, color bands may be extracted from the stained image into separate two-dimensional (2D) arrays, one 2D array (or color channel) for each color component (e.g., red, blue and green channels). Next, a histogram may be computed for each of the color channel (e.g., red, green and blue channels). With the implementation of the K-mean clustering, the pixels in the stained image may be automatically clustered given the predefined number of clusters. For example, the predefined number of clusters may correspond to cytoplasm, nuclei, collagen fibers and background noise. The process may be iteratively repeated until the separation result is optimized with minimized distance within every cluster.

In various example embodiments, a third image corresponding to portal tracts and central veins in the first image 420 may be produced, and a second binarized image (or processed image corresponding to tissue having identified portal tracts and central veins) 422 may be produced based on the third image. Since the portal tracts and central veins are just vessel (e.g., blood flow components), the space inside of the portal tracts and central veins will not be stained and may be displayed as white areas using the clustering technique (K-mean separation). For example, since the first image 420 records the signals of the liver tissue 421 (e.g., signals of hepatocyte cells), portal tracts 424 and central veins 425 may be shown as empty spaces, and thus the segmentation process may select and separate those pixels representing or belonging to portal tracts and central veins based on their intensity values. In various example embodiments, thresholding-based image segmentation (e.g., Otsu-thresholding) and morphological operation-based image pre-processing (e.g., morphological opening/closing) may be applied to the stained image 410 and/or the first image 420 to identify the empty spaces that represent the portal tracts and central veins in order to produce the second binarized image 422. Further, hole-filing operations may be performed to smooth the spaces. The portal tracts and central veins may be further separated by their various sizes and shapes (e.g., portal tracts having larger, irregular holes, while central veins having smaller, rounding holes). Additionally, empty space that are assumed to be sinusoidal spaces with relatively smaller areas and in eclipse shape may be removed prior to further processing. For example, spaces smaller than a predetermined size (e.g. an area of 100 $um^2$) (e.g., size of one hepatocyte cell) and spaces with large major-axis-length to minor-axis-length (assumed to be sinusoidal spaces) may be removed prior to further processing.

In various example embodiments, the second image 430 corresponding to collagen may be processed using contrast enhancement to enhance the signal and further converted to a first binarized image 432, for example, by adaptive thresholding. A first binarized image 432 corresponding to collagen is produced. To produce the first binarized image 432 from the second image 430 which is a color image corresponding to collagen, the second image 430 (e.g., a RGB image) may be converted to gray-scale image using a weighted average technique, and the gray-scale image may be converted to the first binarized image 432 using adaptive thresholding. In some cases, morphological operations such as morphological closing may be used to connect the fragmented collagen fibers and/or means filter such as a despeckle filter may be used to remove noise.

In various example embodiments, the processing 400 further includes a segmentation process to categorize the collagen fibers into various different types of collagen. The segmentation process to categorize the collagen fibers into different types may be performed based on the first and second binarized images 432 and 422. In various example embodiments, various types of collagen including portal, septal and fibrillar collagen were categorized from the first binarized image 432 based on their histo-pathological information with relative location to the portal tracts and central veins from the second binarized image 422. In various example embodiments, the portal, septal and fibrillar collagen may be categorized sequentially based on a plurality of predetermined conditions.

Figure 5:
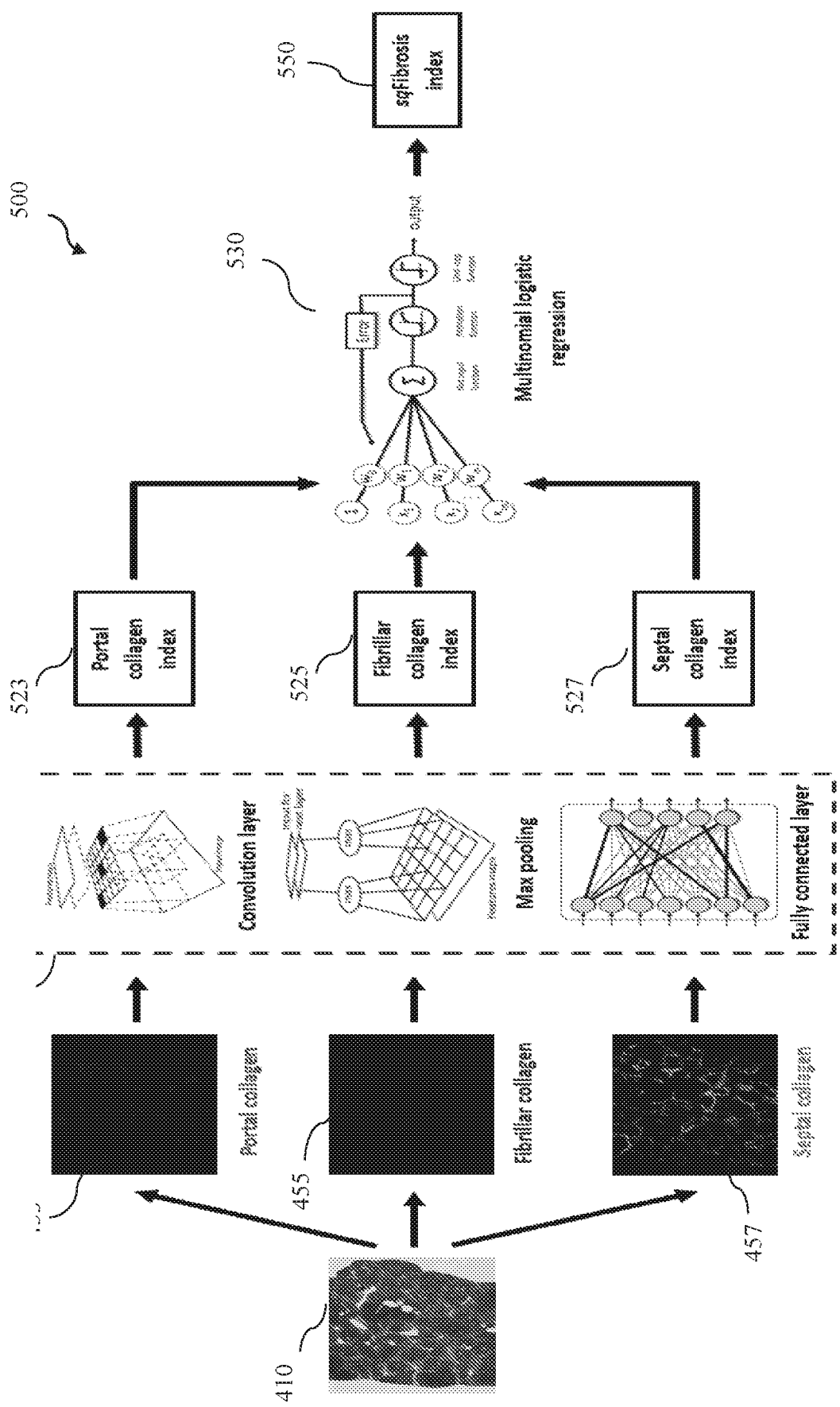
FIG. 5 illustrates a diagram of a framework for assessing fibrosis in a tissue sample according to various example embodiments of the present invention.

As illustrated in FIG. 4, the plurality of different types of collagen images (e.g., portal collagen image 453 corresponding to portal collagen, a fibrillar collagen image 455 corresponding to fibrillar collagen and a septal collagen image 457 corresponding to septal collagen) may be produced based on the first and second binarized images 432 and 422. In various example embodiments, the fibrillar collagen may be selected first for those collagen fibers with areas less than 10 $um^2$, representing the fragmented collagen distributed in the tissue (to produce the first type of collagen image based on collagen in the first binarized image satisfying a predetermined size condition). For example, based on histopathological knowledge, collagen fibers with area less than 10 $um^2$ may be taken to be (or regarded as) fibrillar collagen. Other than a small area size, the fibrillar collagen, for example, are often fragmented, isolated collagen distributed either in the peri-cellular or peri-sinusoidal space, and may be identified or selected based on its distribution. Next, for the portal collagen, pixels from the boundary of the portal tracts and central veins may be first selected and a cut-off distance may be chosen to dilate those selected pixels where all the pixels representing the collagen in the first binarized image within the cut-off distance may be considered as pixels representing the portal collagen (to produce the second type of collagen image based on collagen in the first binarized image satisfying a predetermined distance condition with respect to a boundary of the portal tracts and the central veins in the second binarized image). Next, all the remaining collagen may be considered as septal collagen (to produce the third type of collagen image based on collagen in the first binarized image that does not satisfy the predetermined size condition and the predetermined distance condition). The plurality of different types of collagen images each corresponding to a respective type of collagen may contain signal of that type of collagen. It is should be understood that it some cases, a signal for a particular type of collagen (e.g., fibrillar collagen) may be much weaker in comparison with signal of other types of collagen (e.g., portal and septal collagen) and may not be observable by direct visualization from the collagen image (e.g., fibrillar collagen image 455). FIG. 5 illustrates a diagram of a framework 500 for assessing fibrosis in a tissue sample according to various example embodiments of the present invention. A plurality of different types of collagen parameters may be determined based on the plurality of different types of collagen images using a deep neural network 510. A degree of fibrosis in the stained tissue sample may be determined based on the plurality of different types of collagen parameters.

As illustrated in FIG. 5, the plurality of different types of collagen images (e.g., portal collagen image 453, fibrillar collagen image 455 and septal collagen image 457) may be evaluated using a deep learning-based classification model or deep neural network 510 to obtain predicted results (the plurality of different types of collagen parameters) for the plurality of different types of collagen. The plurality of different types of collagen parameters each comprises a quantitative fibrosis value in relation to the corresponding type of collagen of the plurality of different types of collagen in the stained tissue sample. For example, the quantitative fibrosis value may be a collagen fibrosis index. For example, the plurality of different types of collagen parameters (e.g., denoted as 523, 525 and 527 in FIG. 5) may include a first quantitative fibrosis value corresponding to a first type of collagen (e.g. portal collagen), a second quantitative fibrosis value corresponding to a second type of collagen (e.g. fibrillar collagen) and a third quantitative fibrosis value corresponding to a third type of collagen (e.g. septal collagen).

In various example embodiments, the deep neural network 510 may include a plurality of deep neural sub-networks to determine the plurality of different types of collagen parameters based on the plurality of different types of collagen images. The plurality of deep neural sub-networks may be trained separately for respective types of collagen to produce the plurality of different types of collagen parameters. In other words, each deep neural sub-network of the plurality of deep neural sub-networks may be trained for a particular type of collagen and used to determine a collagen parameter for that type of collagen based on a collagen image corresponding to that type of collagen. In various example embodiments, each deep neural sub-network may be a DCNN. For example, three DCNNs may be trained separately to produce the first quantitative fibrosis value corresponding to the first type of collagen, the second quantitative fibrosis value corresponding to the second type of collagen and the third quantitative fibrosis value corresponding to the third type of collagen, respectively. The architecture of each of the CNN may include an input layer and an output layer, as well as multiple hidden layers made of convolutional layers (applying a convolution operation to the input and passing the result to the next layer), activation functions (defining the output of certain node given an input of set of inputs), pooling layers (combining the outputs of neuron clusters at one layer into a single neuron in the next layer), fully connected layers (connecting every neuron in one layer to every neuron in another layer) and classification layers (converting back to the data label). The processed different type of collagen images for various types of collagen fibers may be fed into the respective DCNN, and analyzed with the aforementioned layers, generating a final class label representing the degree of fibrosis for each type of collagen from the respective type of collagen image.

In various example embodiments, the plurality of different types of collagen parameters may be combined to generate a final quantitative fibrosis value or final fibrosis index (herein referred as sqFibrosis index) 550 of the tissue sample to determine a degree of fibrosis in the tissue sample. In various example embodiments, the plurality of different types of collagen parameters may be combined using logistic regression 530, such as multinomial logistic regression, in a non-limiting example.

Figure 6:
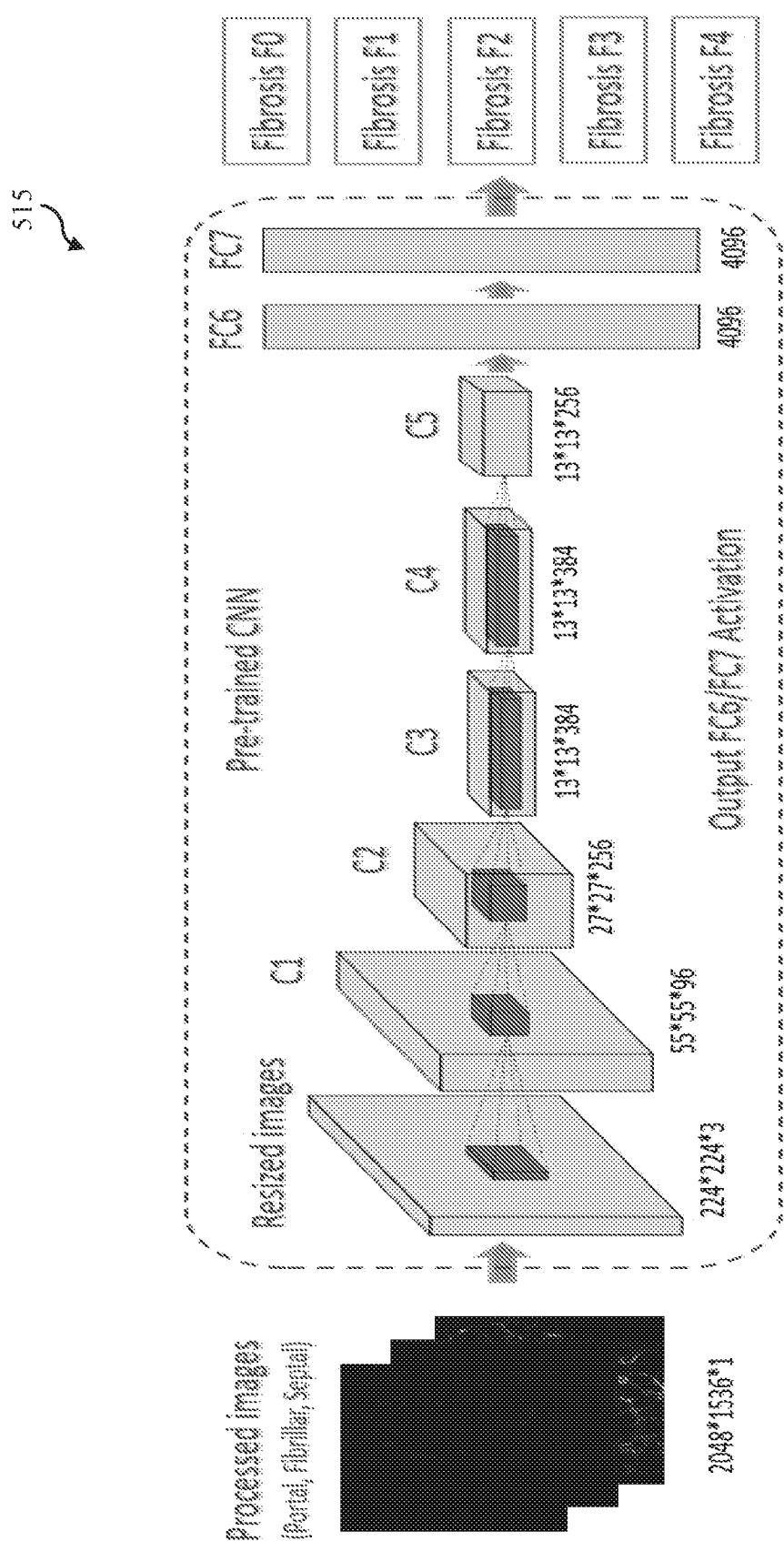
FIG. 6 illustrates a diagram of an exemplary architecture of a deep neural network for assessing fibrosis in a tissue sample according to various example embodiments of the present invention.

FIG. 6 illustrates a diagram of an exemplary architecture of a deep neural sub-network 515 for assessing fibrosis in a tissue sample according to various example embodiments of the present invention. As described, according to various example embodiments, a plurality of the deep neural sub-networks may be provided where each deep neural sub-network of the plurality of the deep neural sub-networks may be used for a particular type of collagen to determine a collagen parameter for that type of collagen based on a collagen image corresponding to that type of collagen. In various example embodiments, the deep neural sub-network 515 may be a DCNN. The deep neural sub-network may include a plurality of convolution layers, max pooling layers and fully connected layers. In various example embodiments, for each type of collagen, the deep neural sub-network 515 may be a pre-trained AlexNet-CNN used for training and testing purposes. In various example embodiments, the deep neural sub-network may be a 7-layered AlexNet-CNN. For example, the deep neural sub-network may be an adapted seven-layered AlexNet algorithm for computer-aided liver fibrosis scoring. For example, Hoo-Chang, S. et al. Deep Convolutional Neural Networks for Computer-Aided Detection: CNN Architectures, Dataset Characteristics and Transfer Learning. *IEEE transactions on medical imaging* 35, 1285-1298, doi:10.1109/TMI.2016.2528162 (2016), discloses an exemplary CNN, which may be adapted and implemented for determining a collagen parameter for a type of collagen based on a collagen image corresponding to that type of collagen, the content of which being hereby incorporated by reference in its entirety for all purposes.

In various example embodiments, each CNN may include one input layer, seven hidden layers (five convolution layers, C1-C5, and two fully connected layers, FC6-FC7) and one output layer using batch stochastic gradient descent, with specific values for momentum and weight decay. In an example implementation in relation to liver fibrosis assessment, the input and output layers of the original AlexNet-CNN network may be replaced accordingly for liver fibrosis assessment in the adapted deep neural sub-network. For example, in the adapted deep neural sub-network, the basic structure of the deep learning neuron network may be maintained while the input and outputs are replaced. For example, the input layer may be used to feed the deep neural sub-network with the different types of collagen images, while the output layer (e.g., last few layers of convolution and fully connected layers) are used to generate a collagen parameter for a respective type of collagen image.

In various example embodiments, the deep neural network (e.g., each deep neural sub-network of the plurality of the deep neural sub-networks) may be trained based on a transfer learning technique. Desautels, T. et al. Using Transfer Learning for Improved Mortality Prediction in a Data-Scarce Hospital Setting. *Biomedical informatics insights* 9, 1178222617712994, doi:10.1177/1178222617712994 (2017); Sharma, H., Zerbe, N., Klempert, I., Hellwich, O. & Hufnagl, P. Deep convolutional neural networks for automatic classification of gastric carcinoma using whole slide images in digital histopathology. *Computerized medical imaging and graphics: the official journal of the Computerized Medical Imaging Society* 61, 2-13, doi:10.1016/j.compmedimag.2017.06.001 (2017); and Krizhevsky, A., Sutskever, I. & Hinton, G. E. in *Proceedings of the 25th International Conference on Neural Information Processing Systems—Volume* 1 1097-1105 (Curran Associates Inc., Lake Tahoe, Nevada, 2012), for example, describes using transfer learning approach for a deep neural network, the content of which being hereby incorporated by reference in their entirety for all purposes. For example, transfer learning is a machine learning method where a model developed for a task is reused as the starting point for a model on a second task. In various example embodiments, the deep neural network may be pre-trained by a very large number of training datasets worldwide using weakly or even irrelevant image sources using the transfer learning technique. In the transfer learning technique using a pre-trained model, first a source model may be selected. In relation to selecting the source model, a pre-trained source model is chosen from available models. In an exemplary implementation, the AlexNet model that was previously trained on large and challenging datasets may be included in the pool of candidate models from which to choose. Next, the selected source model may be reused. For example, the selected pre-trained source model may be used as the starting point for a model on the second task of interest (e.g., liver fibrosis classification). This may involve using all or parts of the model, depending on the modeling technique used. Optionally, the selected source model may be tuned. For example, the selected source model may need to be adapted or refined on the input-output pair data available for the task of interest. It has been found that the pre-trained deep neural network by transfer learning approach may automatically and accurately stage liver fibrosis without feature extraction.

The plurality of different types of collagen images (e.g., processed portal collagen image 453, fibrillar collagen image 455 and septal collagen image 457) may be resized and duplicated to fit as input images into respective CNN trained for each of the portal, fibrillar and septal collagen. In various example embodiments, the processed portal, fibrillar and septal collagen images may be resized and duplicated to 224×224×3 pixels to fit into the respective CNN as input images. In various example embodiments, each CNN may further include two max pooling layers of size 2×2 pixels after the first and second convolution layers where the size and number of filters of the first and second convolution layers are 11×11×3 pixels, 96 and 5×5×96 pixels, 256, respectively. Each CNN may include another three convolution layers (e.g., third, fourth and fifth convolution layers) where the size and number of filters may be 3×3×256 pixels, 384 and 3×3×384 pixels, 384 and 3×3×384 pixels, 256, respectively. The convolution layers may be implemented before a third max pooling layer. Each of the CNN may further include sixth and seventh hidden layers which may be 4096-dimension fully connected layers where the input matrix is transformed into a vector for Softmax activation function through General MATRIX Vector Multiply (GEMV) approach. In various example embodiments, morphological and/or textural features extracted from the deep neural network may be used as input for non-deep learning-based algorithms. During feature extraction, disease patterns are extracted either at the cellular or tissue-level to measure changes in morphological characteristics or to classify the collagen image to grade the disease. Features at the cellular level focus on quantifying the properties of individual cells disregarding any potential spatial relationship that might exist between cells. For single cells, morphological, textural, fractal, and/or intensity-based features may be extracted. Features at the tissue level quantify the distribution of cells across the tissue; these features capture spatial information or the gray-level dependency of pixels. For tissues, textural, fractal, and/or topological features may be extracted. The non-deep learning algorithms are more computational-efficient and less time consuming. It is also more relevant to the pathological interpretation as it correlates with the pathological review process.

In various example embodiments, the final output layer of each deep neural sub-network of the plurality of deep neural sub-networks may be configured to output a quantitative fibrosis value in relation to a respective type of collagen based on the collagen image corresponding to that type of collagen.

Various non-limiting examples of the framework for assessing fibrosis in a tissue sample according to various example embodiments of the present invention is provided as follows:

Establishment of sqFibrosis Index

To combine all collagen index (portal, fibrillar and septal indices) to a final sqFibrosis index, multinomial logistic regression (MLR) may be used. For example, a MLR is described in Lee, K., Ahn, H., Moon, H., Kodell, R. L. & Chen, J. J. Multinomial logistic regression ensembles. *Journal of biopharmaceutical statistics* 23, 681-694, doi: 10.1080/10543406.2012.756500 (2013), the content of which being hereby incorporated by reference in its entirety for all purposes. MLR may be a generalization of normal logistic regression which can create multiple discrete outcomes (for various fibrosis scoring systems). To calculate the fibrosis index for one tissue sample, all the other tissue samples from a specimen may be used as the training set. The probability that the sample belongs to one of stages from 0 to 4 may be predicted from the trained MLR model. In various example embodiments, the fibrosis indices from various types of collagen may be used as new feature inputs for MLR, and a matrix, p, of coefficient estimates may be obtained for a multinomial logistic regression of the nominal responses in fibrosis classes on the predictors in feature space. The coefficients express both the effects of the predictor variables on the relative risk and the log odds of being in one category versus the reference category. Once the probabilities of the given image corresponding to different classes of fibrosis degree is obtained from the plurality of different types of collages images corresponding to various types of collagen respectively, a final index (sqfibrosis index) may be determined (or calculated) using Equation 1 as follows:

$$\text{index} = \alpha \Sigma p_i * E_i, \; i=0, 1, 2, 3, 4, \qquad \text{(Equation 1)}$$

where $p_i$ is the predicted probability of stage i of fibrosis, $E_i$ is the expected value of each stage and $\alpha$ is a scale factor to normalize the index into certain range. In a non-limiting example, $\alpha$ may be set to ¼ so that the index is a continuous variant located in the range from 0 to 1.

Tissue Sample and Image Acquisition of Tissue Samples

In various example embodiments, stained tissue samples may be obtained for assessment as described above. Additionally, the stained tissue samples may be used for training of the deep neural network. In various example embodiments, the tissue samples may be obtained according to, for example, a Thioacetamide (TAA)-induced animal model for assessing liver fibrosis in rats. For example, all the protocols for assessing or studying TAA-induced liver fibrosis rat models were reviewed and approved by the Biological Resource Centre (BRC) Institutional Animal Care and Use Committee (IACUC). In various example embodiments, twenty rats were randomly separated into six groups, representing six time points in relation to treatment of the rats with TAA. The six groups representing six time points may include a group without drug treatment, and groups treated with TAA for 4, 6, 7, 8, and 12 weeks respectively. For example, liver samples or specimens from the left lateral lobe of each animal may be formalin-fixed, paraffin-embedded, and sectioned into slices of 5 µm. Masson Trichrome (MT) staining may be performed on the liver specimens to obtain the stained tissue samples. Additionally, the MT staining may be performed to obtain stained tissue samples for histological examination. Stained images of the stained tissue samples may be further obtained by imaging such as using direct bright field imaging. For example, the samples for training and testing sqFibrosis index may be imaged by a bright field microscope. Image acquisition may be performed with a 4× objective on stained sections of the tissue samples for the bright field microscope. In an example implementation, to cover most areas of the sample, four images may be acquired for each sample with image size of 12 $mm^2$ (4×3 mm) using the bright field microscope. The four images may be used as separate samples.

Further, scoring may be performed by an experienced pathologist using the Metavir fibrosis staging system for comparison with predictions of fibrosis in tissue samples using the framework 500 as described above. sqFibrosis showed similar trends in the groups of regression and progression patients as evaluated by Metavir fibrosis staging system, exhibiting a high correlation with Metavir fibrosis scores. Accordingly, the framework 500 which includes deep learning-based algorithms can automatically quantify liver fibrosis progression in the TAA-induced fibrotic rat livers using collagen stains on the tissue samples, which is commonly available in the clinical settings; and can score different stages of liver fibrosis with high sensitivity and specificity.

Figure 7:
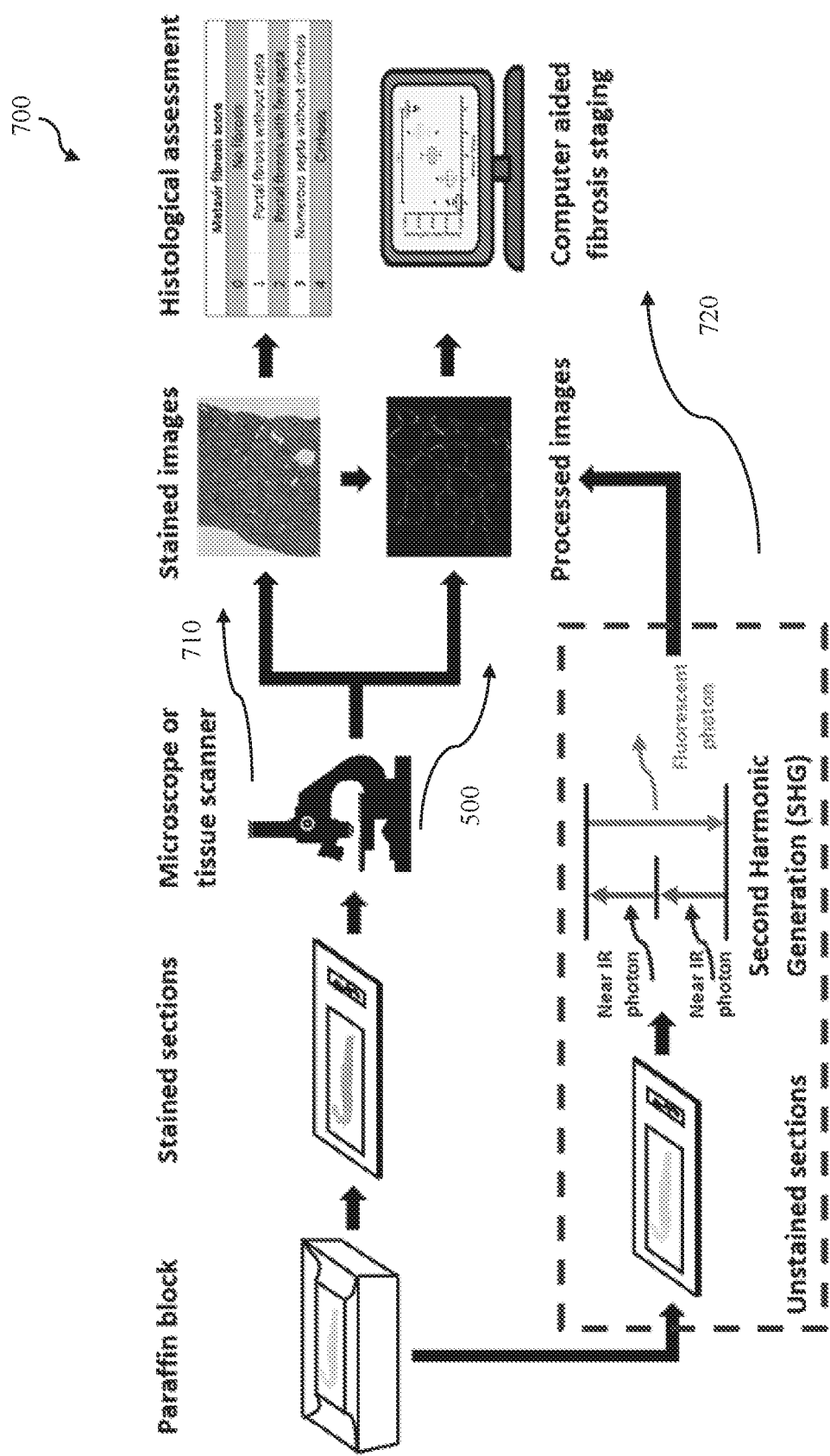
FIG. 7 illustrates a flow diagram of various conventional techniques, and a technique or framework according to various example embodiments of the present invention for assessing fibrosis in a tissue sample.

FIG. 7 illustrates a flow diagram 700 of various conventional techniques 710 and 720 and a technique or framework 500 according to various example embodiments of the present invention for assessing fibrosis in a tissue sample. The conventional technique 720 is a stain-free multiphoton microscopy-based qFibrosis approach. For example, collagen features may be extracted from an unstained section of the tissue sample using second harmonic generation/two-photon excitation fluorescence (SHG/TPEF) microscopy technique. However, the multi-photon microscope is not commonly available in clinics or laboratories, which makes the clinical applicability of these techniques difficult, in addition to variations that are present due to the imaging process and use of the multi-photon microscope. In contrast to previous techniques, the sqFibrosis index obtained by framework 500 provides a fully-quantitative, computer-aided liver fibrosis staging for the assessment of fibrosis in biopsy-based tissue samples, particularly using stained tissue samples. In addition, the framework 500 may have improved clinical applicability compared to conventional techniques since a standard light microscope may be used.

Statistical Analysis

In various example embodiments, Kruskal-Wallis (KW) tests may be used to estimate the statistical differences within sqFibrosis index and collagen proportionate area (CPA) for Metavir fibrosis stages. Two-tailed Wilcoxon rank-sum test may be performed to estimate the statistical differences of sqFibrosis index and CPA between different Metavir stages. For example, statistical significance level may be set as p<0.05.

Figure 8A:
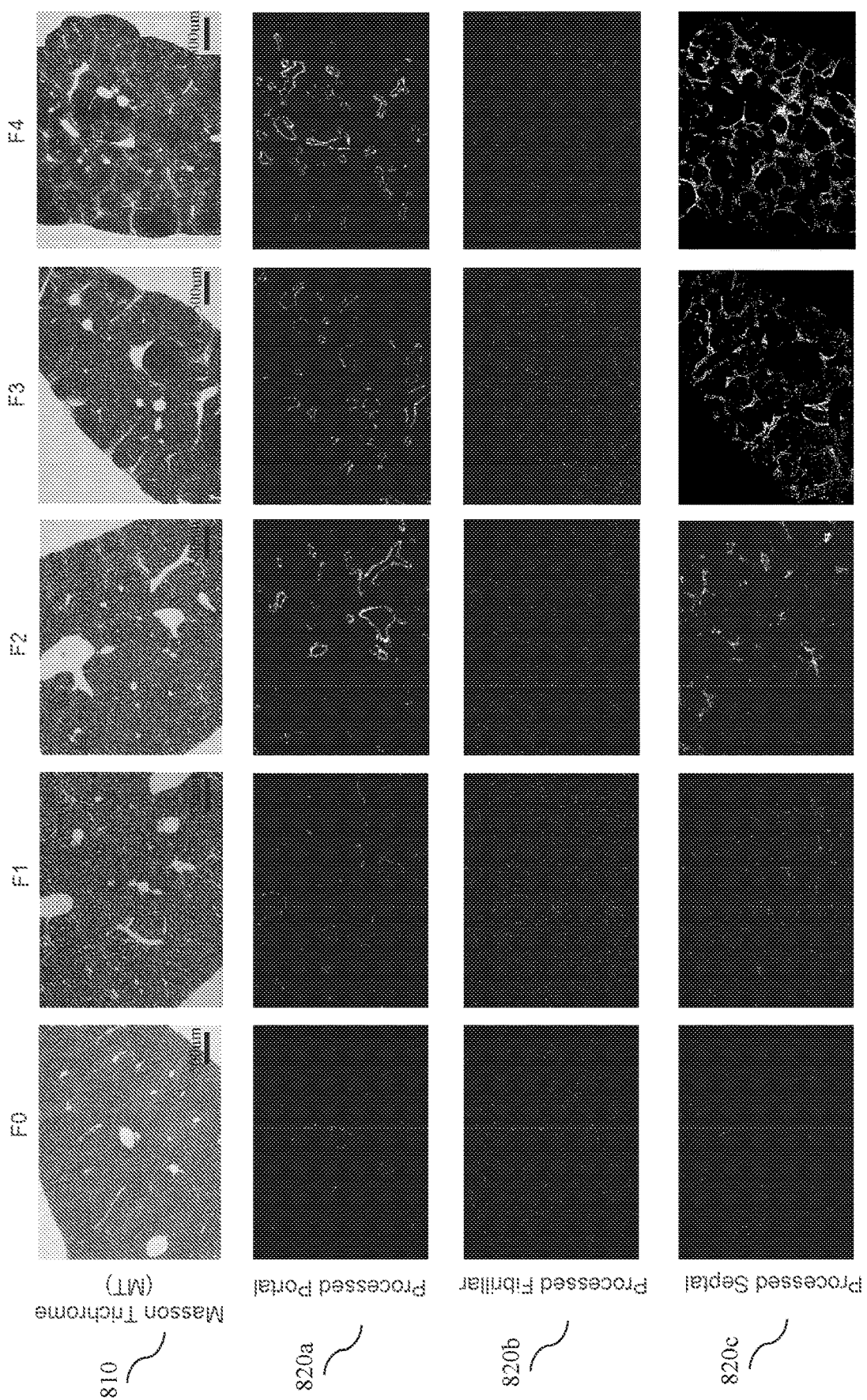
FIGS. 8A-8C illustrate an exemplary comparison of assessment using sqFibrosis and collagen proportionate area (CPA) of changes in collagen patterns from images of stained tissue samples in various stages of liver fibrosis.
Figure 8B:
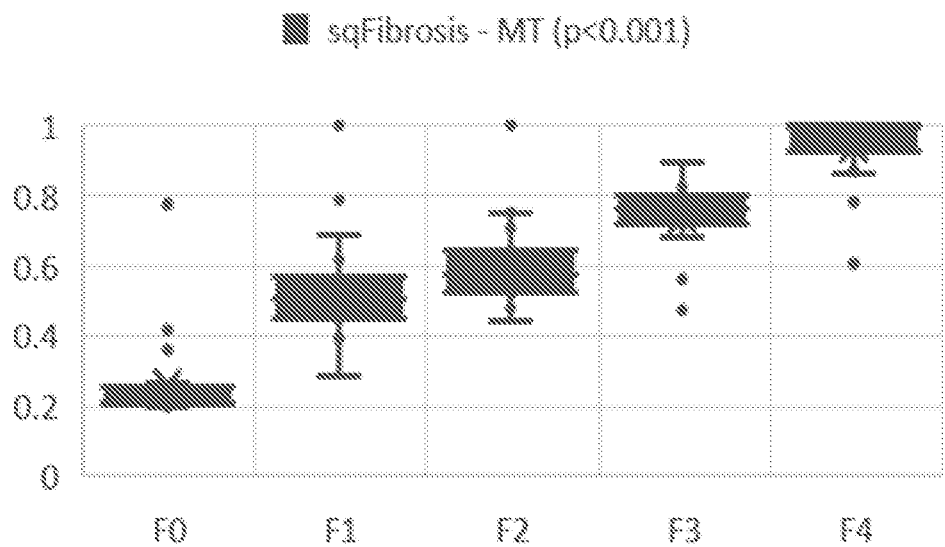
Figure 8C:
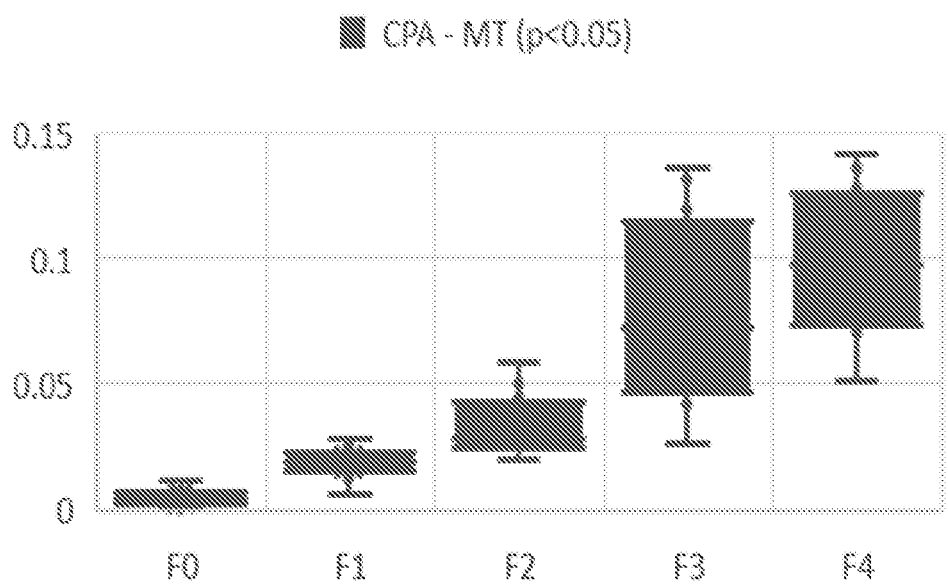

FIGS. 8A-8C illustrate an exemplary comparison of assessment using sqFibrosis and CPA of changes in collagen patterns from images of stained tissue samples in various stages of liver fibrosis. For example, FIG. 8A shows a representation of changes in collagen patterns in chronic liver disease for animals based on Metavir staging system in stained images 810 of stained tissue sample and processed images 820 of the stained images (e.g., processed portal collagen images 820a, processed fibrillar collagen images 820b and processed septal collagen images 820c) in various stages of fibrosis (e.g., F0, F1, F2, F3, F4). In a non-limiting example illustration, the portal, fibrillar and septal collagen may be denoted in colors such blue, red and green, respectively (not shown). For example, in different stages of fibrosis, the processed images may include different patterns of collagen fibers visualized in blue, red and/or green. FIGS. 8B and 8C respectively show changes of sqFibrosis index and CPA with fibrosis progression between the various stages for animals. sqFibrosis index may be able to reliably recapitulate various fibrosis staging systems, as it can identify differences between all stages in animal samples (p<0.001), with superior performance, for example, in comparison to CPA (p=0.152). sqFibrosis values increased with fibrosis progression and showed significant differences between all the stages of liver fibrosis. CPA showed drastic changes only in late stages and could not differentiate between early stages (stages 1 and 2).

Figure 9:
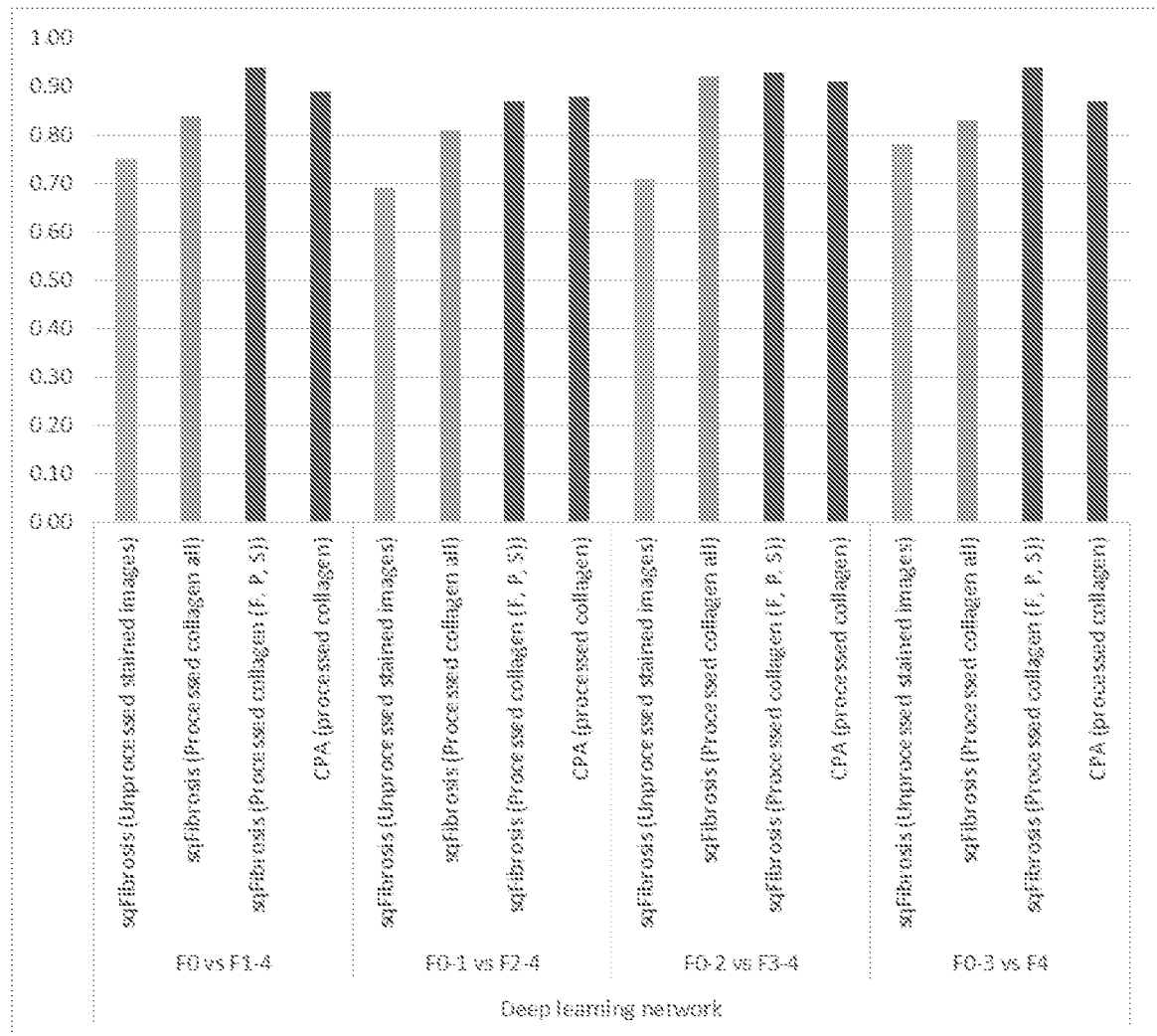
FIG. 9 shows a graph illustrating performance evaluation for deep learning models of sqFibrosis index using unprocessed stained images, processed collagen images without categorization into different types, and processed collagen images with categorization into different types of collagen, and CPA.

FIG. 9 shows a graph illustrating performance evaluation for deep learning models of sqFibrosis index using unprocessed stained images, processed collagen images without categorization into different types, and processed collagen images with categorization into different types of collagen (e.g., portal, fibrillar and septal collagen) and collagen proportionate area (CPA). sqFibrosis index is more reliable with an area under the ROC (AUROC) value of 0.94 for fibrosis detection; AUROC value of 0.87 for significant fibrosis detection, AUROC value of 0.93 for advanced fibrosis detection, and AUROC value of 0.94 for cirrhosis detection in the case where processed collagen images with categorization into different types of collagen is used for the deep learning models. On the other hand, in the case sqFibrosis index is determined using unprocessed stained images, an AUROC value of 0.75 for fibrosis detection, AUROC value of 0.69 for significant fibrosis detection, AUROC value of 0.71 for advanced fibrosis detection, and AUROC value of 0.78 for cirrhosis detection was obtained. As for the case sqFibrosis index is determined using processed collagen images without categorization, an AUROC value of 0.84 for fibrosis detection, AUROC value of 0.81 for significant fibrosis detection, AUROC value of 0.92 for advanced fibrosis detection, and AUROC value of 0.83 for cirrhosis detection was obtained. Accordingly, determination of sqFibrosis index using processed collagen images with categorization into different types of collagen for the deep learning models allows for sensitive grading of fibrosis score for animal samples. sqFibrosis index also demonstrates superior performance to CPA (AUROC value of 0.89 for fibrosis detection; AUROC value of 0.88 for significant fibrosis detection, AUROC value of 0.91 for advanced fibrosis detection, and AUROC value of 0.87 for cirrhosis detection).

Figure 10A:
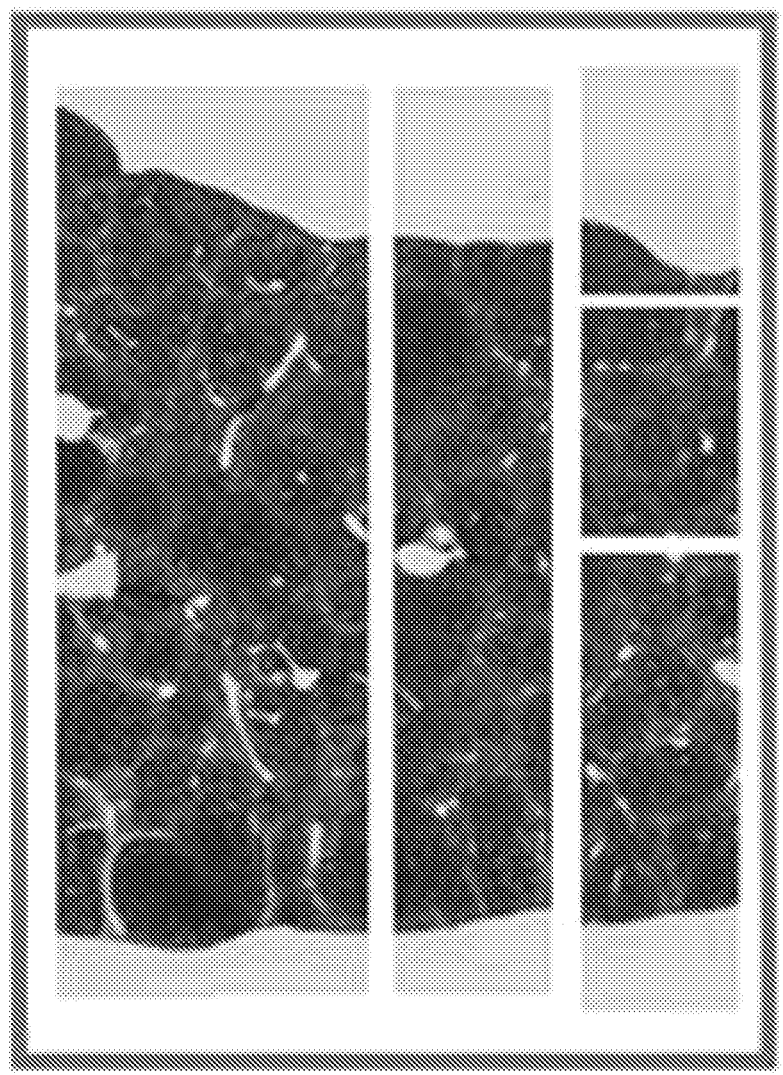
FIGS. 10A-10B respectively illustrate stained images of stained tissue sample for various sample sizes from an animal study and AUROC values of sqFibrosis and CPA for the various sample sizes assessed based on different stages of fibrosis in the tissue sample.
Figure 10B:
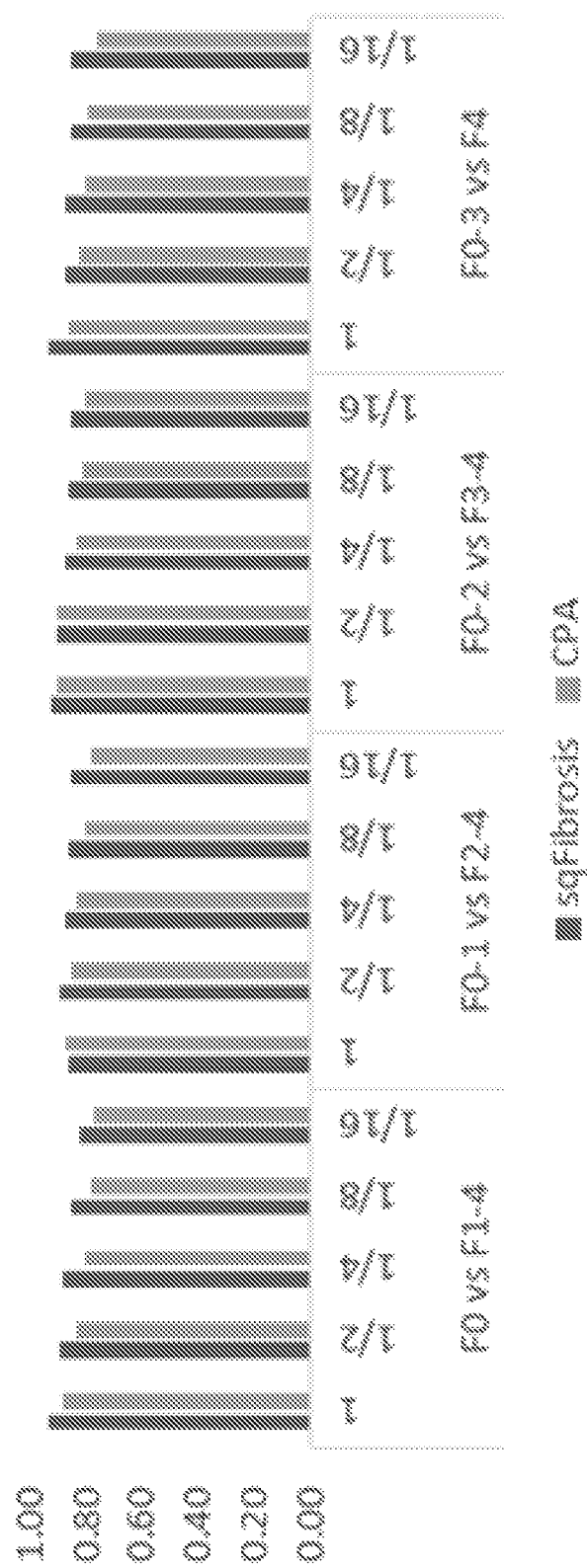
Figure 11A:
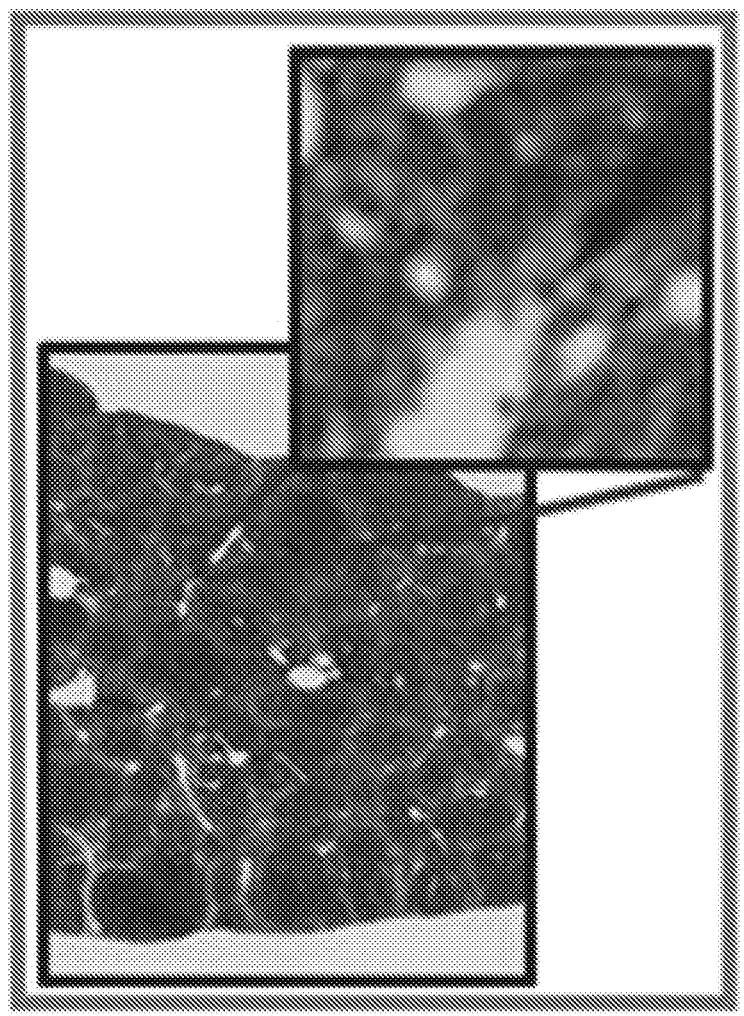
FIGS. 11A-11B respectively illustrate stained images of stained tissue sample for various image resolutions from an animal study and AUROC values of sqFibrosis and CPA for the various image resolutions assessed based on different stages of fibrosis in the tissue sample.
Figure 11B:
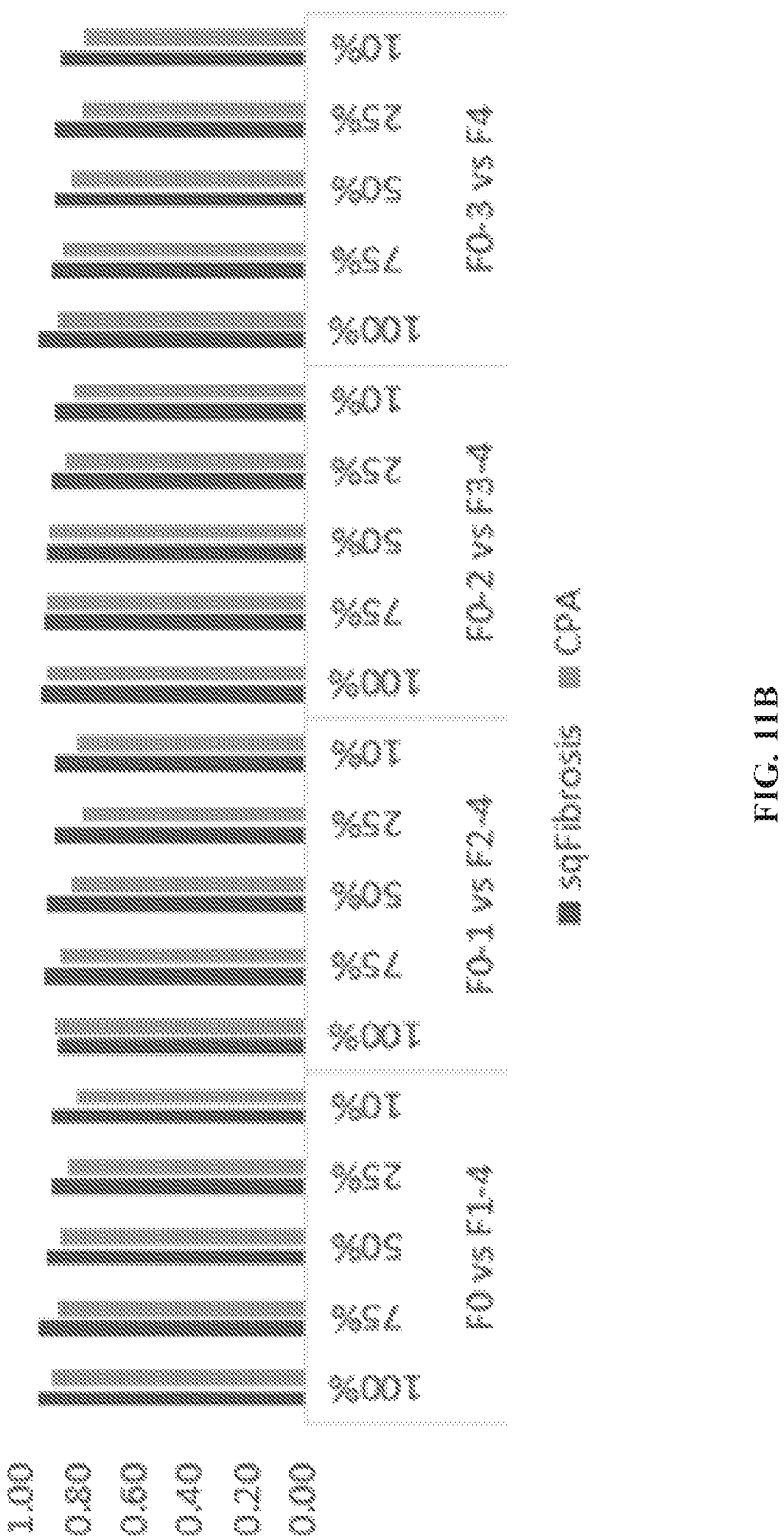
Figure 12A:
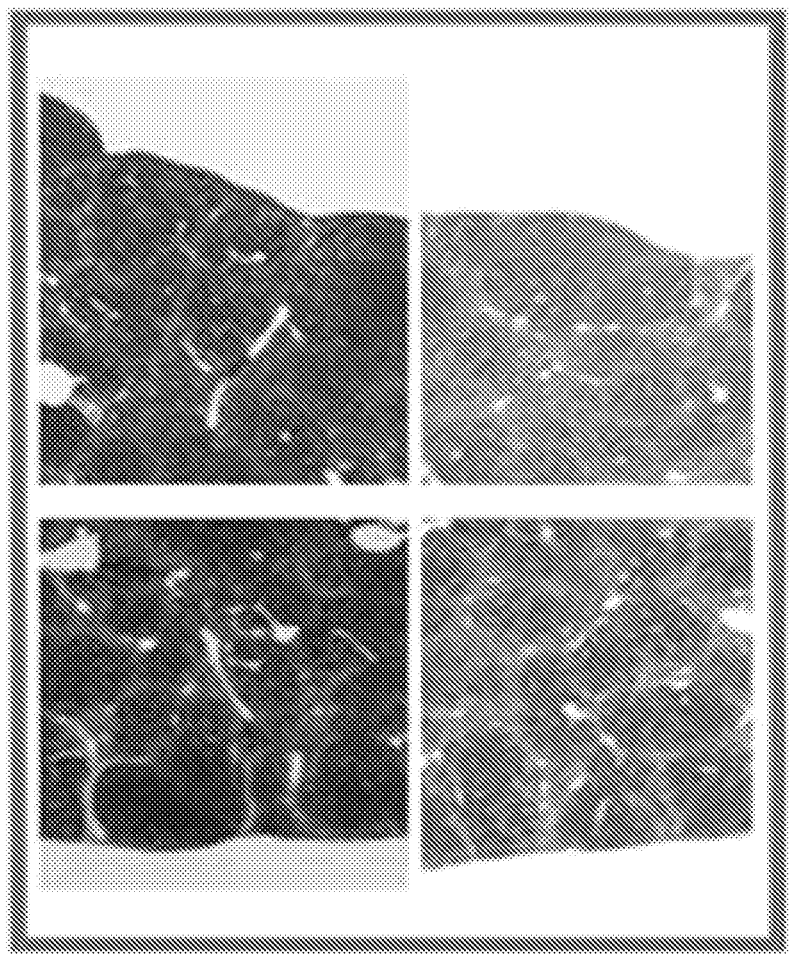
FIGS. 12A-12B respectively illustrate stained images of stained tissue sample for various image intensities from an animal study and AUROC values of sqFibrosis and CPA for the various image intensities assessed based on different stages of fibrosis in the tissue sample.
Figure 12B:
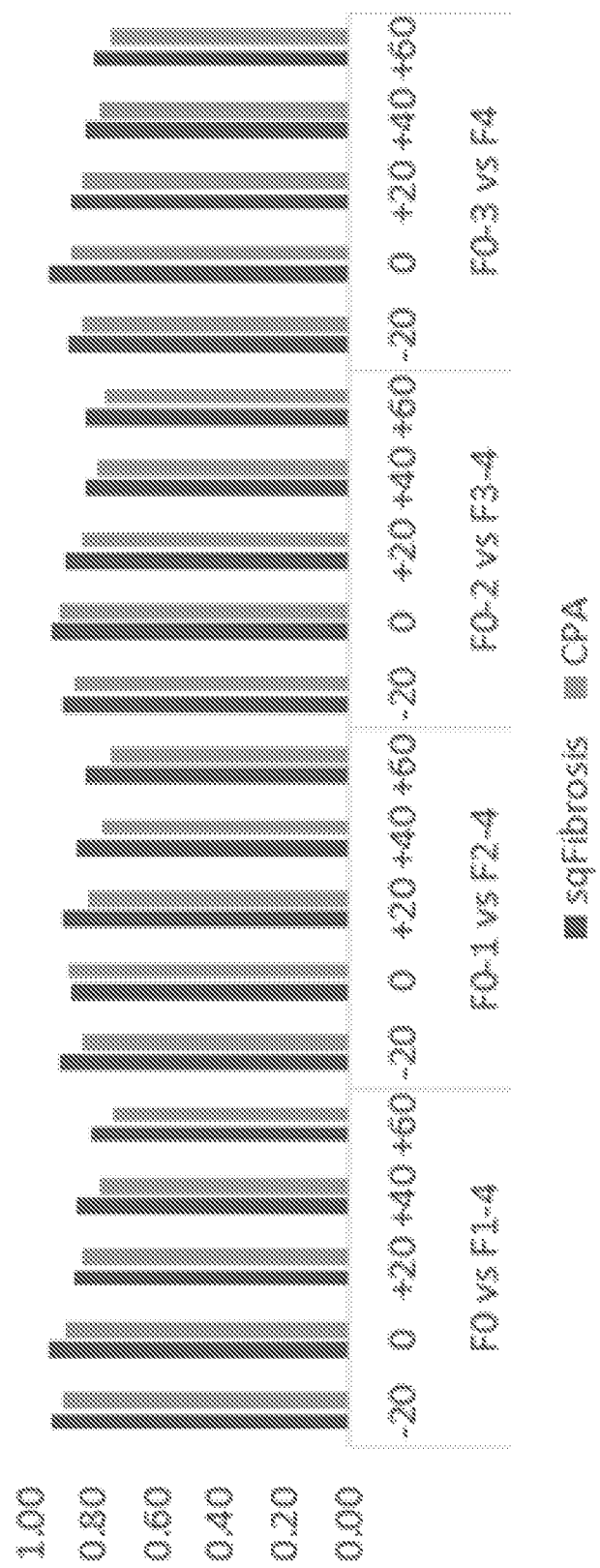

Sample error is a major limitation when applying quantification methods such as CPA. To assess the sensitivity of sqFibrosis index to sampling error, a proof-of-concept demonstration was performed with animal samples. Various image sizes, image resolutions and image intensities were generated and examined to simulate samples of varying qualities. FIGS. 10A-10B respectively illustrate stained images of stained tissue sample for various sample sizes from an animal study and AUROC values of sqFibrosis and CPA for the various sample sizes assessed based on different stages of fibrosis in the tissue sample. FIGS. 11A-11B respectively illustrate stained images of stained tissue sample for various image resolutions from an animal study and AUROC values of sqFibrosis and CPA for the various image resolutions assessed based on different stages of fibrosis in the tissue sample. FIGS. 12A-12B respectively illustrate stained images of stained tissue sample for various image intensities from an animal study and AUROC values of sqFibrosis and CPA for the various image intensities assessed based on different stages of fibrosis in the tissue sample. The AUROC values of sqFibrosis index decreased slightly along with the reduction in sample size, resolution and intensity. CPA achieved similar AUROC values as sqFibrosis index in standard condition; however, the AUROC values of CPA decreased drastically when the sample size, resolution and intensity were reduced.

It has been found that while conventional semi-automated learning algorithms are useful for liver fibrosis scoring, deep learning-based algorithm is more promising as it automatically finds the features and calculates the weight of each feature through their contribution, which would be more time-efficient and cost-saving. Inevitably, large datasets and complex training neural networks are required for deep learning-based algorithms, such requirement may be compensated by using transfer learning from weakly or even irrelevant image sources. The sqFibrosis index according to embodiments of the present invention enables the assessment of important features. For example, the image pre-processing of the stained image enables the categorization of various types of collagen, which enables further feature computation and classification using deep learning/transfer learning approach. This determines the minimally required set of features for classification, and hence reduces the number of parameters in the deep learning models. sqFibrosis index may be further evaluated using other scoring systems such as the Ishak staging and Beijing P-I-R classification for the analysis of intra-stage cirrhotic detection and pre-/post-treatment monitoring from clinical perspective.

In various example embodiments, the sqFibrosis index, a deep learning-based algorithm using pre-trained deep neural network (e.g., AlexNet-CNN), may automatically improve fibrosis staging accuracy and throughput, thus quantitatively stage liver fibrosis using existing collagen stained liver samples readily available in less sophisticated clinical or lab settings as well as hospitals. Additionally, the stained tissue samples are low cost, easily comprehensible and well documented. A transfer learning approach using weakly or even irrelevant image sources may facilitate solving the requirement of large datasets for deep learning-based algorithms. This advantageously addresses problems in techniques such magnetic resonance imaging (MRI) and computerized tomography (CT) images on liver fibrosis which demand the use of a large training dataset and biopsy sample images typically do not meet this need. This computer-aided and automated quantification of scoring liver fibrosis stages may be generalized to the design of high performance classification systems for other medical imaging tasks since there are large repertoire/database of such histological stained samples already available worldwide.

While embodiments of the invention have been particularly shown and described with reference to specific embodiments, it should be understood by those skilled in the art that various changes in form and detail may be made therein without departing from the scope of the invention as defined by the appended claims. The scope of the invention is thus indicated by the appended claims and all changes which come within the meaning and range of equivalency of the claims are therefore intended to be embraced.

What is claimed is:

1. A computer-implemented method of assessing fibrosis in a tissue sample using at least one processor, the method comprising:
    obtaining a stained image of a stained tissue sample, the stained tissue sample being stained in relation to collagen therein;
    producing a plurality of different types of collagen images based on the stained image, the plurality of different types of collagen images corresponding to a plurality of different types of collagen, respectively;
    determining a plurality of different types of collagen parameters based on the plurality of different types of collagen images using a deep neural network; and
    determining a degree of fibrosis in the stained tissue sample based on the plurality of different types of collagen parameters.

2. The method of claim 1, wherein said producing a plurality of different types of collagen images comprises:
    producing a first image corresponding to tissue in the stained image; and
    producing a second image corresponding to collagen in the stained image.

3. The method of claim 2, wherein said producing a plurality of different types of collagen images further comprises:
    producing a third image corresponding to portal tracts and central veins in the first image.

4. The method of claim 3, wherein said producing a plurality of different types of collagen images further comprises:
    producing a first binarized image based on the second image;
    producing a second binarized image based on the third image; and
    producing the plurality of different types of collagen images based on the first and second binarized images.

5. The method of claim 4, wherein the first and second images are produced based on K-mean clustering.

6. The method of claim 4, wherein the plurality of different types of collagen images comprises a first type, a second type, and a third type of collagen images, and said producing the plurality of different types of collagen images based on the first and second binarized images comprises:
    producing the first type of collagen image based on collagen in the first binarized image satisfying a predetermined size condition;
    producing the second type of collagen image based on collagen in the first binarized image satisfying a predetermined distance condition with respect to a boundary of the portal tracts and the central veins in the second binarized image; and
    producing the third type of collagen image based on collagen in the first binarized image that does not satisfy the predetermined size condition and the predetermined distance condition.

7. The method of claim 1, wherein the plurality of different types of collagen comprises portal collagen, fibrillar collagen and septal collagen.

8. The method of claim 1, wherein the plurality of different types of collagen parameters each comprises a quantitative fibrosis value in relation to the corresponding type of collagen of the plurality of different types of collagen in the stained tissue sample.

9. The method of claim 1, wherein the degree of fibrosis in the tissue sample is determined based on the different types of collagen parameters using a multinomial logistic regression.

10. The method of claim 1, wherein the deep neural network comprises a plurality of deep neural sub-networks corresponding to the plurality of different types of collagen respectively, wherein each deep neural sub-network of the plurality of deep neural sub-networks is configured to output a quantitative fibrosis value in relation to a respective type of collagen.

11. A system for assessing fibrosis in a tissue sample, the system comprising:
a memory; and
at least one processor communicatively coupled to the memory and configured to:
obtain a stained image of a stained tissue sample, the stained tissue sample being stained in relation to collagen therein;
produce a plurality of different types of collagen images based on the stained image, the plurality of different types of collagen images corresponding to a plurality of different types of collagen, respectively;
determine a plurality of different types of collagen parameters based on the plurality of different types of collagen images using a deep neural network; and
determine a degree of fibrosis in the stained tissue sample based on the plurality of different types of collagen parameters.

12. The system according to claim 11, wherein said produce a plurality of different types of collagen images comprises:
producing a first image corresponding to tissue in the stained image; and
producing a second image corresponding to collagen in the stained image.

13. The system according to claim 12, wherein said produce a plurality of different types of collagen images further comprises:
producing a third image corresponding to portal tracts and central veins in the first image.

14. The system according to claim 13, wherein said produce a plurality of different types of collagen images further comprises:
producing a first binarized image based on the second image;
producing a second binarized image based on the third image; and
producing the plurality of different types of collagen images based on the first and second binarized images.

15. The system according to claim 14, wherein the first and second images are produced based on K-mean clustering.

16. The system according to claim 14, wherein the plurality of different types of collagen images comprises a first type, a second type, and a third type of collagen images, and said produce the plurality of different types of collagen images based on the first and second binarized images comprises:
producing the first type of collagen image based on collagen in the first binarized image satisfying a predetermined size condition;
producing the second type of collagen image based on collagen in the first binarized image satisfying a predetermined distance condition with respect to a boundary of the portal tract and/or the central vein in the second binarized image; and
producing the third type of collagen image based on collagen in the first binarized image that does not satisfy the predetermined size condition and the predetermined distance condition.

17. The system according to claim 11, wherein the plurality of different types of collagen comprises portal collagen, fibrillar collagen and septal collagen.

18. The system according to claim 11, wherein the plurality of different types of collagen parameters each comprises a quantitative fibrosis value in relation to the corresponding type of collagen of the plurality of different types of collagen in the stained tissue sample.

19. The system according to claim 11, wherein the degree of fibrosis in the tissue sample is determined based on the different types of collagen parameters using a multinomial logistic regression.

20. A computer program product, embodied in one or more non-transitory computer-readable storage mediums, comprising instructions executable by at least one processor to perform a method of assessing fibrosis in a tissue sample, the method comprising:
obtaining a stained image of a stained tissue sample, the stained tissue sample being stained in relation to collagen therein;
producing a plurality of different types of collagen images based on the stained image, the plurality of different types of collagen images corresponding to a plurality of different types of collagen, respectively;
determining a plurality of different types of collagen parameters based on the plurality of different types of collagen images using a deep neural network; and
determining a degree of fibrosis in the stained tissue sample based on the plurality of different types of collagen parameters.

* * * * *